(12) United States Patent
Coffee et al.

(10) Patent No.: US 6,684,879 B1
(45) Date of Patent: *Feb. 3, 2004

(54) INHALER

(75) Inventors: Ronald Alan Coffee, Haslemere (GB); Alastair Bruce Pirrie, Oxford (GB); David Neville Davies, Oxford (GB)

(73) Assignee: Battelle Memorial Institute, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/868,266

(22) PCT Filed: Dec. 17, 1999

(86) PCT No.: PCT/GB99/04303

§ 371 (c)(1), (2), (4) Date: Aug. 9, 2001

(87) PCT Pub. No.: WO00/35524

PCT Pub. Date: Jun. 22, 2000

(30) Foreign Application Priority Data

Dec. 17, 1998 (GB) .............................. 9827856

(51) Int. Cl.[7] .............................................. A61M 11/00
(52) U.S. Cl. ............................. 128/200.14; 128/200.16; 128/203.12
(58) Field of Search ....................... 128/203.12, 203.15, 128/203.17, 203.26, 203.27, 203.28, 200.14, 200.16; 604/58

(56) References Cited

U.S. PATENT DOCUMENTS

| 1,958,406 | A | * | 5/1934 | Darrah ........................ 361/228 |
| 3,198,193 | A | * | 8/1965 | Schwartzman et al. 128/203.22 |
| 3,255,750 | A | * | 6/1966 | Schwartzman et al. 128/203.22 |
| 3,724,459 | A | * | 4/1973 | Congro ................... 128/203.22 |
| 4,702,415 | A | * | 10/1987 | Hughes .......................... 239/8 |
| 4,795,330 | A |   | 1/1989 | Pavey |
| 4,829,996 | A | * | 5/1989 | Noakes et al. ......... 128/200.14 |
| 5,347,998 | A | * | 9/1994 | Hodson et al. ........ 128/200.23 |
| 5,487,378 | A | * | 1/1996 | Robertson et al. ..... 128/200.16 |
| 5,511,726 | A |   | 4/1996 | Greenspan et al. |
| 5,616,123 | A |   | 4/1997 | Cheikh |
| 5,645,051 | A | * | 7/1997 | Schultz et al. ......... 128/203.15 |
| 5,655,517 | A | * | 8/1997 | Coffee ................... 128/203.12 |
| 5,728,088 | A |   | 3/1998 | Magruder |

(List continued on next page.)

FOREIGN PATENT DOCUMENTS

| DE | 3446466 | 7/1986 |
| DE | 19534280 | 3/1996 |
| EP | 0234842 | 9/1987 |
| GB | 1385521 | 2/1975 |
| GB | 1569707 | 6/1980 |
| WO | WO 9440441 | 12/1996 |
| WO | WO 9803267 | 1/1998 |
| WO | WO 9818561 | 5/1998 |
| WO | WO 99/42153 | * 8/1999 ............ 128/203.15 |

*Primary Examiner*—Weilun Lo
*Assistant Examiner*—Michael Mendoza
(74) *Attorney, Agent, or Firm*—Frost Brown Todd LLC

(57) ABSTRACT

An inhaler has a housing containing a chamber (1a) providing a reservoir (8) for liquid providing an active ingredient to be supplied to a liquid outlet (10a). First and second electrodes are spaced apart (11 and 12) with the first electrode being spaced apart (11 and 12) with the first electrode being provided at or adjacent the liquid outlet (10a). A voltage supply (5, 7) is activated in response to air flowing through an air inlet (30) of the housing to provide a potential difference between the first and second electrodes (11 and 12) to create an electric field for causing comminution of liquid issuing from the liquid supply outlet (10a) to produce a stream of electrically charged comminuted matter for supply to the nasal passages of a user via an outlet (4) of the housing.

50 Claims, 12 Drawing Sheets

U.S. PATENT DOCUMENTS

| | | | | |
|---|---|---|---|---|
| 5,840,074 A | | 11/1998 | Ayer | |
| 5,915,377 A | * | 6/1999 | Coffee | 128/200.16 |
| 6,068,199 A | * | 5/2000 | Coffee | 239/3 |
| 6,076,519 A | * | 6/2000 | Johnson | 128/200.14 |
| 6,105,571 A | * | 8/2000 | Coffee | 128/200.14 |
| 6,105,877 A | * | 8/2000 | Coffee | 239/3 |
| 6,318,640 B1 | * | 11/2001 | Coffee | 239/3 |
| 6,386,195 B1 | * | 5/2002 | Coffee | 128/200.14 |
| 6,394,086 B1 | * | 5/2002 | Barnes et al. | 128/203.15 |
| 6,457,470 B1 | * | 10/2002 | Coffee | 128/200.14 |
| 6,503,481 B1 | * | 1/2003 | Thurston et al. | 424/45 |

\* cited by examiner

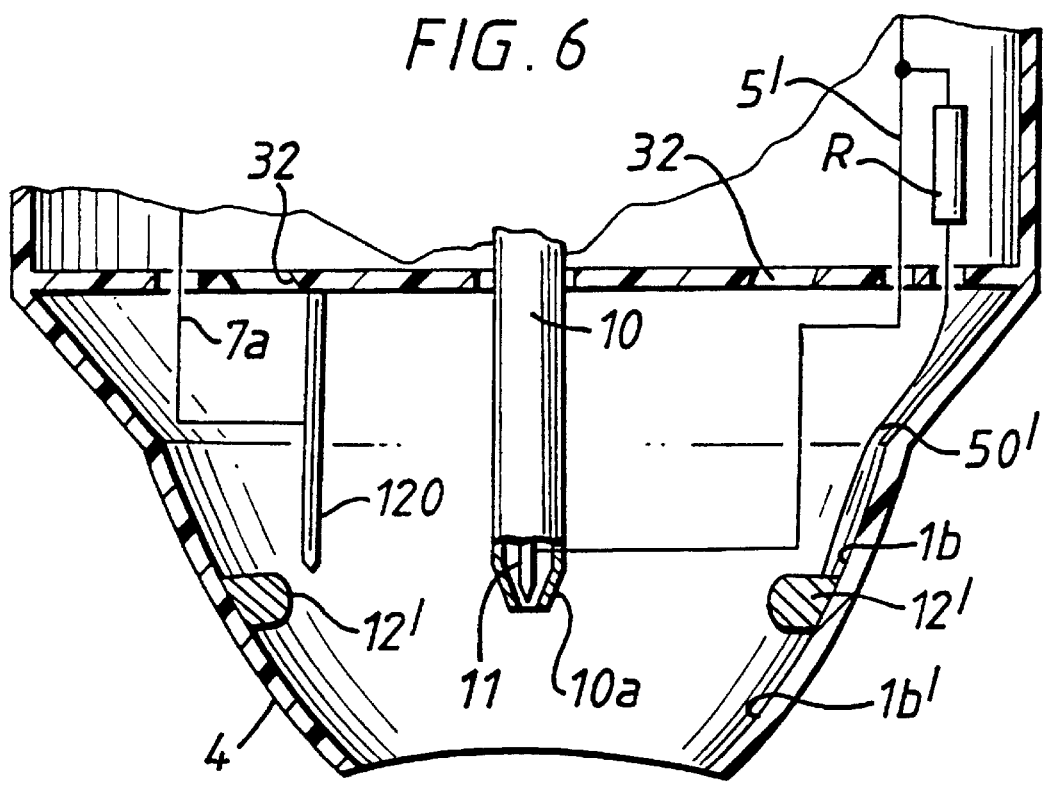
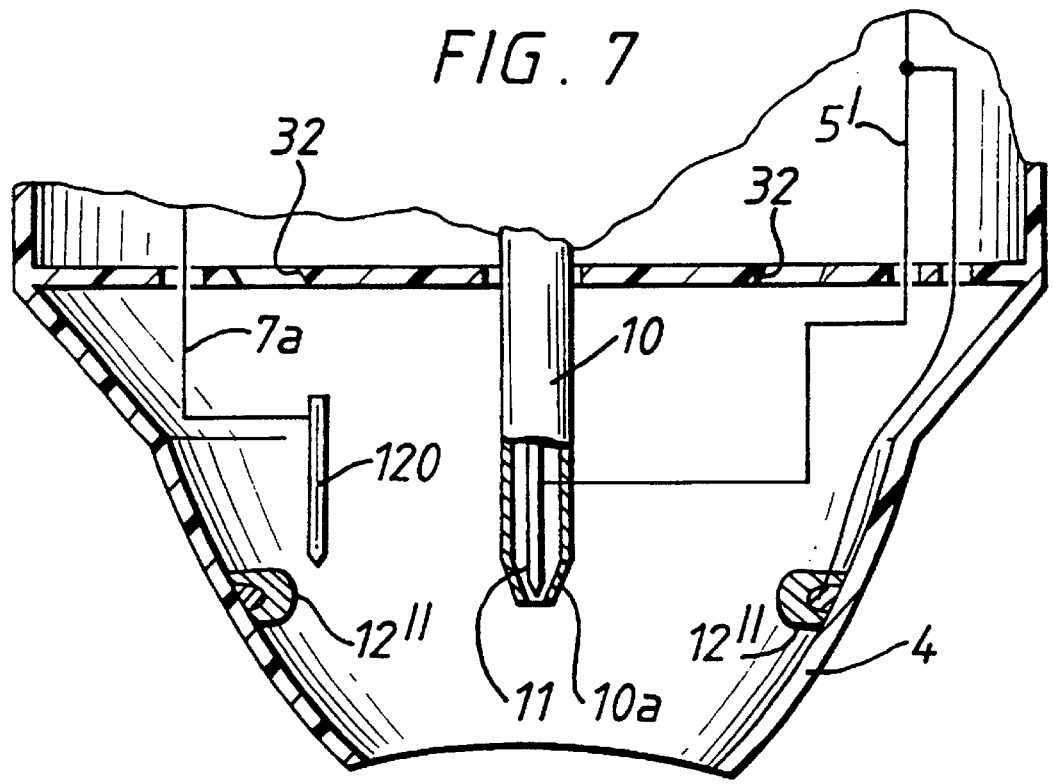

FIG. 13
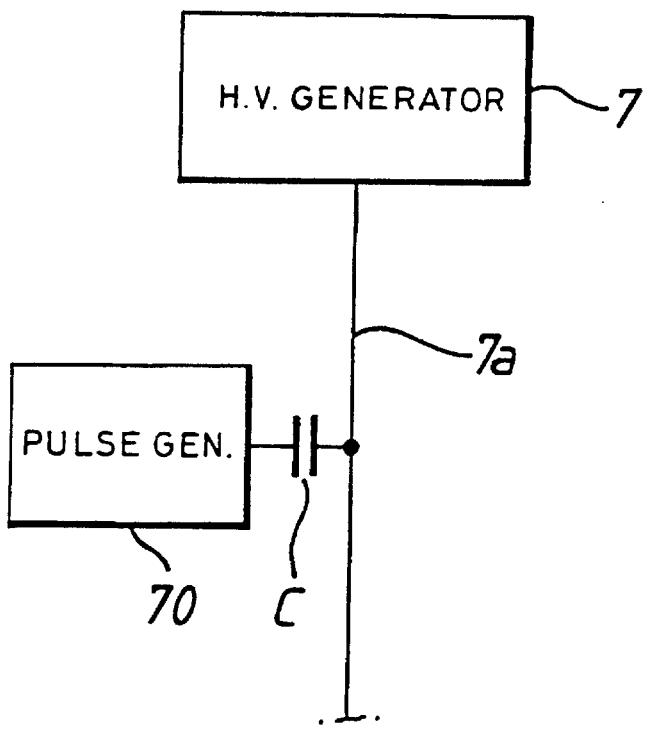
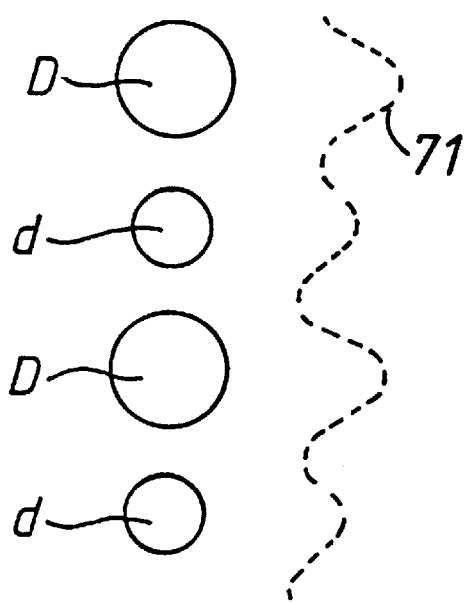
FIG. 14

INHALER

This invention relates to an inhaler for enabling delivery of an active ingredient to the nasal passages.

Conventionally, nasal inhalers are used for the supply of decongestants such as oxymetazoline and the like. The nasal passages are also a good way of supplying drugs and other medicaments into the bloodstream for treatment of ailments which are not specific to the nasal passages.

Conventional hydraulic/pump action nasal inhalers fire or eject large droplets of liquid into the nose. These droplets are polydispersed, that is they have a broad spectrum of sizes. The deposition of such droplets is primarily due to their own inertia which can lead to a very patchy distribution of the liquid. Indeed excessive deposition in one region can lead to the droplets coalescing and flowing out of a nostril or down the back of the throat which can cause an unpleasant taste or, worse, lead to detrimental side effects as a result of the drug being delivered to the digestive or pulmonary system.

It is an aim of the present invention to provide a device which enables satisfactory and efficient supply of a substance such as a medicament or other active ingredient to the nasal mucosa avoiding deposition in non-target regions such as the lungs or the stomach.

A process for producing comminuted matter known as electrohydrodynamic comminution is described in detail in, for example, GB-A-1569707. In this process, a dispersed spray or cloud of comminuted matter such as liquid droplets which are all of substantially the same size (monodispersed) is produced by subjecting liquid emerging from an outlet to an electric field.

The device described in GB-A-1569707 is large, produces highly charged droplets and is intended primarily for spraying of crops.

Inhalers have been proposed that exploit electrohydrodynamic comminution because they have the advantage, unlike conventional inhalers, of producing a monodispersed (substantially all the same size) mist or cloud of droplets so that the droplets may be targeted more accurately. However, because the conventional wisdom is that it is difficult, if not impossible, to spray electrically charged material into a cavity, previous attempts at producing inhalers using electrohydrodynamic techniques require that the comminuted matter be electrically discharged before inhalation. For example, EP-A-0234842 teaches that it is necessary to discharge the resulting comminution before inhalation to prevent it being deposited only on the wet conductive surfaces immediately inside the mouth or throat.

The present inventors have, surprisingly, found that, by a combination of electrohydrodynamic, discharging or partial discharging techniques and aerodynamic forces on the resultant comminution, an inhaler can be provided which generates by electrohydrodynamic means electrically charged comminuted matter which can be inhaled so as to deposit evenly onto the conductive inner surface of the nasal passages from whence an active ingredient carried by the comminution can be rapidly absorbed into the bloodstream without being inhaled into the pulmonary system.

In one aspect, the present invention provides an inhaler having electrohydrodynamic comminution means arranged to be activated by inhalation by a user, which facilitates entrainment of electrically charged comminuted matter into the air flow and thence into the nasal passages of the user.

In one aspect the present invention provides an inhaler having electrohydrodynamic comminution means with the electrode or electrodes of the comminution means being shielded from the user so that the user cannot make direct electrical contact with the electrodes.

In one aspect the present invention provides an inhaler wherein the material to be inhaled is electrohydrodynamically produced and the electrical charge and/or size of the comminuted material, generally droplets, are/is controlled so that the material can be deposited evenly into the nasal passages but supply to the pulmonary system or the back of the throat is prevented, thereby enabling the inhaler to be used for the supply to the nasal passages of medicaments which may produce unpleasant or undesirable effects if they were supplied to the pulmonary or digestive system.

In one aspect the present invention provides an inhaler having a supply of liquid carrying an active ingredient, means for supplying the liquid to an outlet and means for subjecting liquid issuing from the outlet to an electrical field sufficient to cause comminution of the liquid to produce electrically charged comminuted matter for inhalation by the user, the liquid or liquids being selected so as to control the manner in which active ingredient in the electrically charged comminuted matter is released when the electrically charged comminuted matter is deposited in the nasal passages. The liquid may be an oil or alcohol-based formulation allowing rapid supply of the active ingredient into the bloodstream via the surfaces of the nasal passages. As another possibility, the liquid may be such that the resulting comminuted matter has a gel-like structure enabling continued release of the active ingredient.

In one aspect the present invention provides an inhaler having means for subjecting liquid issuing from an outlet to an electric field sufficient to cause comminution of the liquid and means for causing electrically charged comminuted matter to be deposited onto the surfaces of the nasal passages. The latter means may comprise means for causing or facilitating an air flow through the inhaler which entrains the charged comminuted matter such an air flow may be generated by inhalation by a user, by artificial means such as a pump or a combination of both of these.

In one aspect, the present invention provides an inhaler having comminution means arranged to provide an electric field which has a strength which reduces rapidly in the direction of liquid flow from liquid supply means enabling liquid comminuted by the electric field to be easily entrained in an air flow path from the inhaler into a nostril of a user during use.

In one aspect, the present invention provides an inhaler having means for supplying liquid to an outlet and means for subjecting liquid issuing from the outlet to an electrical field sufficient to cause comminution of liquid issuing from the outlet, and means for generating an electrical potential at the one of the first and second electrodes most remote from the liquid outlet, said means for generating the electrical potential comprising means for generating an ion current for indirectly charging said one electrode.

In this aspect, the ion current generating means may comprise a further electrode located adjacent the one electrode and means for providing a high resistance path to earth from said one electrode. The high resistance path to earth may be provided by an actual resistor in series with said one electrode or, for example, a resistive or semiconductive coating on said one electrode. Indirect charging of said one electrode reduces the possibility of deposition of comminuted matter onto said one electrode because any electrically charged comminuted matter which approaches said one electrode will be at least partially electrically discharged by the generated ions. Furthermore, a more even deposition or greater penetration within the nasal passages should be achieved because of the at least partial discharge of some of the comminuted matter by the ion generating means.

In one aspect, the present invention provides an inhaler having means for supplying liquid to a comminution site and electrical current limiting means for limiting the supply of electrical current to the comminution site. The current-limiting means may comprise a dielectric or semi-insulating coating or sleeve or a high resistance coupled in the path from a high capacitance high voltage source to an electrode. Otherwise, a low capacitance high voltage source, such as a piezoelectric voltage source, may be used.

In one aspect, the present invention provides an inhaler capable of supplying opposite polarity comminutions to the nasal passages.

In one aspect, the present invention provides a dispensing device, which may be an inhaler, having means for supplying liquid to an outlet, means for subjecting liquid issuing from the outlet to an electrical field sufficient to cause comminution of liquid issuing from the outlet and means for controlling the size of individual elements of the comminuted matter, for example droplets, in the resulting comminution.

Embodiments of the present invention will now be described, by way of example, with reference to the accompanying drawings, in which:

FIG. 1 illustrates schematically use of an inhaler in accordance with the present invention;

FIG. 2 shows a diagrammatic, part-cross-sectional view of an embodiment of an inhaler in accordance with the present invention;

FIG. 3 shows a block schematic electrical diagram for the inhaler shown in FIG. 2;

FIG. 4 shows a part-cross-sectional view, on an enlarged scale, of part of the inhaler shown in FIG. 2 to show one example of an electrohydrodynamic comminution site for the inhaler shown in FIG. 2;

FIG. 5 shows a part-cross-sectional view, on an enlarged scale, of part of the inhaler shown in FIG. 2 to show another example of an electrohydrodynamic comminution site for the inhaler shown in FIG. 2;

FIG. 6 shows a part-cross-sectional view, on an enlarged scale, of part of a further embodiment of an inhaler in accordance with the present invention;

FIG. 7 shows a part-cross-sectional view, on an enlarged scale, of part of another embodiment of an inhaler in accordance with the present invention;

FIG. 8 shows very schematically another example of an inhaler embodying the present invention using a compressed airflow for activation;

FIGS. 9*a* to 9*d* show droplet spectrums with FIG. 9*a* showing a droplet spectrum for an inhaler embodying the invention and FIGS. 9*b* to 9*d* showing droplet spectrums for various forms of conventional inhaler;

FIG. 10 shows a diagrammatic part cross-sectional view similar to FIG. 2 of another embodiment of an inhaler in accordance with the present invention;

FIG. 11 shows a diagrammatic part cross-sectional view similar to FIG. 2 of another embodiment of an inhaler in accordance with the present invention;

FIG. 12 shows, on an enlarged scale, part of the inhaler shown in FIG. 2 to illustrate a modification thereof;

FIG. 13 shows very schematically a further modification of an embodiment of an inhaler in accordance with the present invention;

FIG. 14 is a diagram for illustrating the operation of an inhaler having the modification shown in FIG. 13;

FIG. 15 shows a part cross-sectional enlarged view of part of another embodiment of an inhaler in accordance with the invention; and FIG. 16 shows a part cross-sectional enlarged view of part of another embodiment of an inhaler in accordance with the invention.

As illustrated schematically in FIG. 1, an inhaler 1 embodying the invention is intended primarily for use as a pocket-sized, hand-held device which is actuated by a user to enable delivery of an active ingredient, drug or active ingredient into the nostril of the user. For example, the inhaler may be arranged to deliver a decongestant such as oxymetazoline to the nasal passages or to deliver drugs or other medicaments such as insulin or triptans (for example Elitriptan) into the bloodstream via the nasal mucosa. The inhaler may also be used to deliver flu vaccines such as Flumist (a product being developed by Aviron of Mountain View, Calif. USA) which is arranged to be effective in the relatively low temperature environment of the nasal mucosa.

The inhaler 1 comprises a housing 3. The housing may be made mainly of electrically insulative material such as a plastics material although at least a part of the housing that a user will inevitably touch in use provides an electrically conductive region that enables, as will be described below with reference to FIGS. 2 and 3, an earth connection via the user. The inhaler has an outlet 4 through which liquid droplets to be inhaled are supplied to the user. The outlet 4 is sized and shaped so as to fit snugly against or slightly into the user's nostril so as to make a reasonably air-tight seal. The outlet may be detachable from the housing to allow different sized and shaped outlets to be used so as to enable a snug fit to different sizes of nostrils to enable, for example, use by both adults and children. Although a snug fit is desirable from the viewpoint of efficiency, in practice, it may be sufficient for the inhaler to be placed in close proximity to a nostril.

The inhaler 1 is rotationally symmetric about its longitudinal axis so as to be generally cylindrical. Typically, the housing will be about one inch (25.4 mm) diameter and about 4 to 5 inches (102 to 127 mm) in length.

FIG. 2 illustrates a part sectional view through one example of an inhaler embodying the invention, while FIG. 3 shows a block circuit diagram of components of the inhaler.

As shown in FIG. 2, the housing 3 of the inhaler 1 has an internal wall 3*a* which divides the housing into first and second chambers 1*a* and 1*b*.

In this example, the first chamber accommodates a voltage source 5 in the form of a battery. As shown most clearly in FIG. 3, the positive terminal of the battery 5 is connected via a user-operable switch SW1 to a reset input of a counter 6 and to a further switch SW2. Although not shown in FIG. 2, the negative terminal of the battery 5 is also connected to the electrically conductive region of the housing mentioned above so, as shown schematically in FIG. 3, the user H provides a path to earth (ground). The switch SW1 is a conventional manually operable switch such as, for example, a toggle or push switch. The switch SW2 is arranged to be activated by airflow and will be described in greater detail below. A high voltage generator 7 is coupled to the battery 5 via the switches SW1 and SW2 and a counter 6 which is arranged to be reset by closure of the switch SW1 and which outputs the battery voltage to the high voltage generator positive voltage input until a predetermined count is reached when the output of the counter goes low. The high voltage generator may be a conventional electromagnetic high voltage multiplier of the type supplied by Brandenburg, Astec Europe, of High Street, Wollaston, Stourbridge, West Midlands DY8 4PG, UK, or Start Spellman of Unit 1, Broomers Park, Broomers Hill Lane, Pulborough, West Sussex RH20 2RY, UK. As an alternative, a piezoelectric high voltage source which has a low capacitance may be used.

Figure 4:
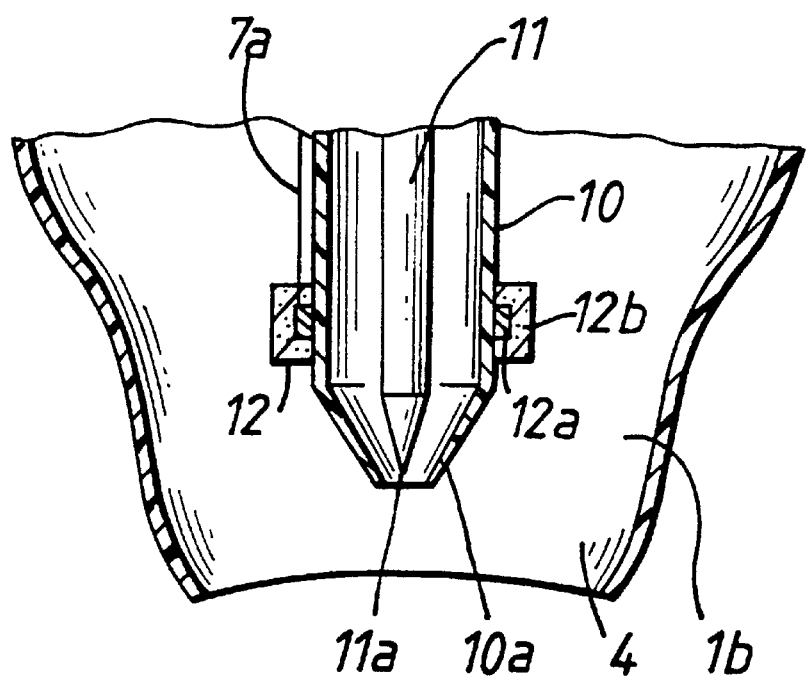
Figure 5:
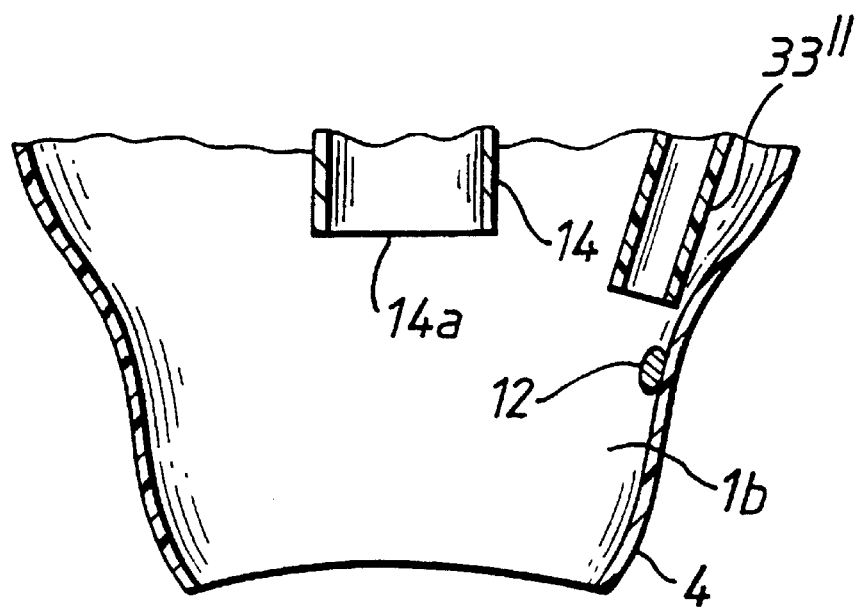

The first chamber 1a also contains a reservoir 8 for the liquid to be dispensed by the inhaler. The reservoir may be formed as a flexible collapsible bag or bellows—type arrangement having a chemically inert interior surface. Alternatively, a piston-like arrangement may be used so that as the liquid is used up, the piston moves with the liquid surface in the chamber so avoiding the possibility of air coming into contact with the liquid in the reservoir. A pump 9 is provided to pump liquid from the reservoir 8 to a liquid supply outlet pipe 10. The pipe is made of an insulating material which does not retain charge for any significant length of time. A suitable material is, for example, polyacetyl or Delrin (Trademark).

The liquid supply pipe 10 has an outlet nozzle 10*a*. A conductive core or rod 11 provided within the liquid outlet pipe terminates adjacent the nozzle outlet 10*a* and provides a first electrode. In this example, the first electrode 11 is coupled to the negative or earth terminal of the battery 5 via line 5'.

The outer surface of the insulative supply pipe 10 carries a second electrode 12 (see FIG. 4) extending around the pipe 10. The second electrode 12 is located so as to be upstream of the tip 11*a* of the first electrode in the direction of the liquid flow through the liquid supply pipe 10. The first electrode 11 may, as shown, be pointed.

In this example, the second electrode 12 comprises a coated electrode having a central conductive core 12*a* which is coupled to a high voltage output 7*a* of the high voltage generator 7 and is encased in a dielectric or semi-insulating coating or sleeve 12*b*. Such a coated electrode is described in, for example, EP-A-0186983. The coating or sleeve may have a resistivity within the range $5\times10^{11}$ to $5\times10^{13}$ Ω cm and a thickness of approximately 2 mm. Suitable coatings are certain grades of sodaglass and phenolformaldehyde/paper composites. Kite brand tubes supplied by Tufnol Limited of Birmingham, England or Paxoline may be used. The core may be formed of, for example, beads of carbon tightly packed within the coating 12*b*. The coating should have a time constant or relaxation time over which it leaks or conducts charge of, typically, approximately $10^{-5}$ seconds. The second electrode 12 may, however, be uncoated.

As can be seen from FIG. 2, the first and second electrodes 11 and 12 are located well within the electrically insulative housing 4 so that the portion 4*a* of the housing defining the chamber 1*b* shields the user from the electrodes so that direct contact by the user with the electrodes is avoided. The outlet 4 is sized so as to prevent a user inserting a finger into the chamber 1*b*. Also, although an electrical shorting is extremely unlikely, this would occur between the first and second electrodes and so would not subject the user to an electrical shock.

The pump 9 is an electrically operated pump and may be, for example, a piezoelectric pump or any other suitable form of electrically or mechanically operated pump. The pump 9 is coupled to the positive terminal of the battery 5 via the switches SW1 and SW2, and the counter 6. A delay circuit 120, for example a conventional capacitor-resistor (CR) network, may be provided between the counter 6 output and the pump so that supply of the voltage necessary to activate the pump 9 is delayed until an electric field sufficient to cause electrohydrodynamic comminution of liquid supplied to the nozzle 10*a* has been established between the first and second electrodes.

The output of the counter 6 is also supplied, as shown in FIG. 3, to an indicator light or buzzer 13.

As shown in FIG. 2, the air flow activated switch SW2 comprises a first electrical contact 20 mounted on a spring biassing arm 21 secured to the inner wall of the housing chamber 1*a*. The switch SW2 has an outer insulative body 22 which is caused by the spring biassing member 21 to block an air inlet 30 provided in the housing 3. An air path from the air inlet 30 to an aperture 32 in the partition member 3*a* is defined by an insulative tubular body 33. An inner wall of the insulative tubular body 33 carries a further electrical contact 34 coupled via conductor 35 to the positive power supply terminal of the high voltage generator 7.

The air path tube 33 may be modified so as to provide air paths 33' coupling to two or more apertures 32 provided in the partition member 3*a* and evenly distributed about the longitudinal axis L as shown in dashed lines in FIG. 2.

To use the inhaler 1, a person first inserts the outlet 4 into or places the outlet snugly against a nostril and then manually actuates the switch SW1 which couples the reset terminal of the counter 6 to the positive supply of the battery 5 and so resets the count of the counter. The user then inhales through their nose as they would if using a conventional inhaler. The air flow resulting from the user inhaling thus causes the contact 20 of the switch SW2 to be moved towards the contact 34 against the biassing force of the spring member 21. Once the contacts 20 and 34 of the switch SW2 make contact, power is supplied to the high voltage generator 7 which supplies the required high voltage, typically 3 to 12 kV (kilovolts) to the second electrode 12 so as to establish the necessary electric field between the first and second electrodes 11 and 12 to provide the electrohydrodynamic comminution site. Once this electric field has been established, the delay circuit 120 provides the necessary electrical power to the pump 9 which then pumps liquid from the reservoir to the outlet nozzle 10*a*.

Liquid issuing from the outlet nozzle 10*a* is electrohydrodynamically comminuted. The separation of the first and second electrodes 11 and 12 in the radial direction (that is perpendicular to the longitudinal axis L) can be relatively small (typically about 1 cm) because the coating on the second electrode enables the two electrodes to be close together whilst suppressing any electrical breakdown of the air in between. This relatively small separation results in a very high strength electric field which drops off or reduces rapidly in the longitudinal direction L. This facilitates entrainment of the resulting charged comminuted matter in the air flow through the tube 33 to the output 4 so reducing the possibility of the electrically charged matter depositing on the inner wall of the chamber 1*b*.

Comminuted matter then issues from the nozzle 4 and is deposited uniformly onto the conductive surface inside the nasal passages.

When a predetermined time since activation of the switch SW1 has passed, that is when the predetermined count is reached, the output from the counter 6 goes low switching off the high voltage generator 7, the pump and the light or buzzer 13. After use, the user then can disable the device by pressing the switch SW1 again to disconnect the voltage source 5.

The counter 6 thus enables the user to be advised when the required dose of medicament has been delivered.

The coating or sleeving of the electrode 12 provides a current limiting effect to prevent excessive or dangerous currents from passing between it and the first electrode 11.

FIG. 5 shows a modification in which the insulative liquid supply pipe and conductive core 10 and 11 of FIG. 2 are replaced by a hollow electrically conductive capillary tube pipe 14 which provides both the first electrode and the outlet 14a. In this case, the second electrode 12 is a discrete uncoated electrode provided on the inner wall of the first chamber so as to be disposed downstream of the end of the first electrode 14 in the direction of liquid flow through the conductive pipe 14. As shown in FIG. 5, the inhaler has an air supply pipe outlet 33" (which may be an extension of the pipe 33' shown in dashed lines in FIG. 2) which causes, in use, an air curtain to be provided in front of the electrode to inhibit deposition of droplets on the electrode 12. This modification may also be made in the arrangement shown in FIG. 2. Although shown as a discrete uncoated electrode, the second electrode 12 may in this case comprise an annular slot electrode or a number of individual electrodes distributed around the inner periphery of the wall of the second chamber 1b. Also, the electrode 12 may be coated as described with reference to FIG. 4 and may be positioned slightly upstream or adjacent the first electrode. In this case, when an electrical field sufficient to cause electrohydrodynamic comminution is established between the first and second electrodes 14a and 12, multiple jets or cones will generally be formed at the end of the conductive pipe 14.

Figure 9A:
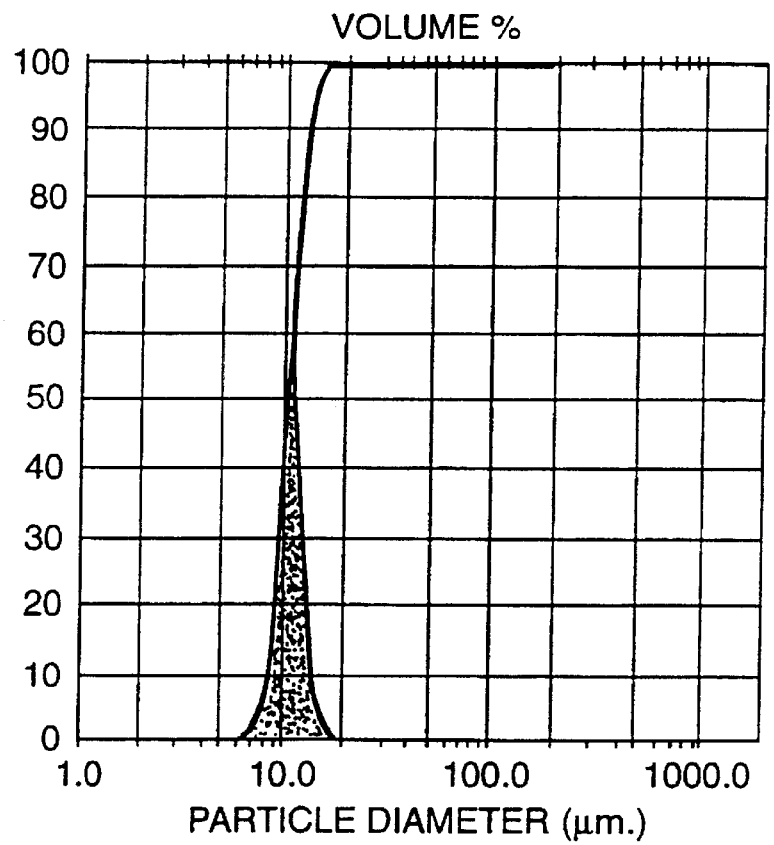
Figure 9B:
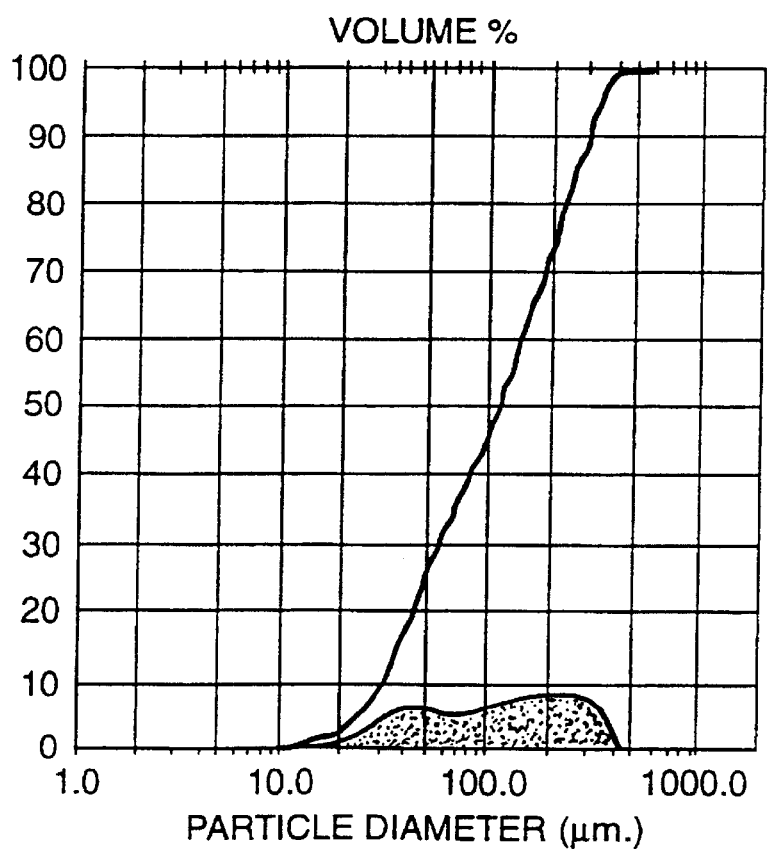
Figure 9C:
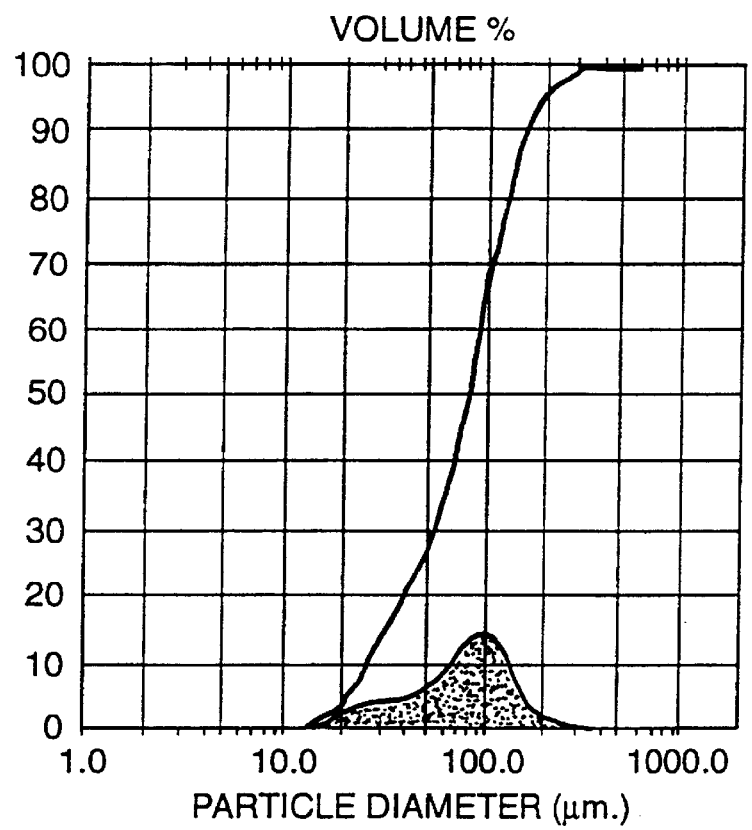
Figure 9D:
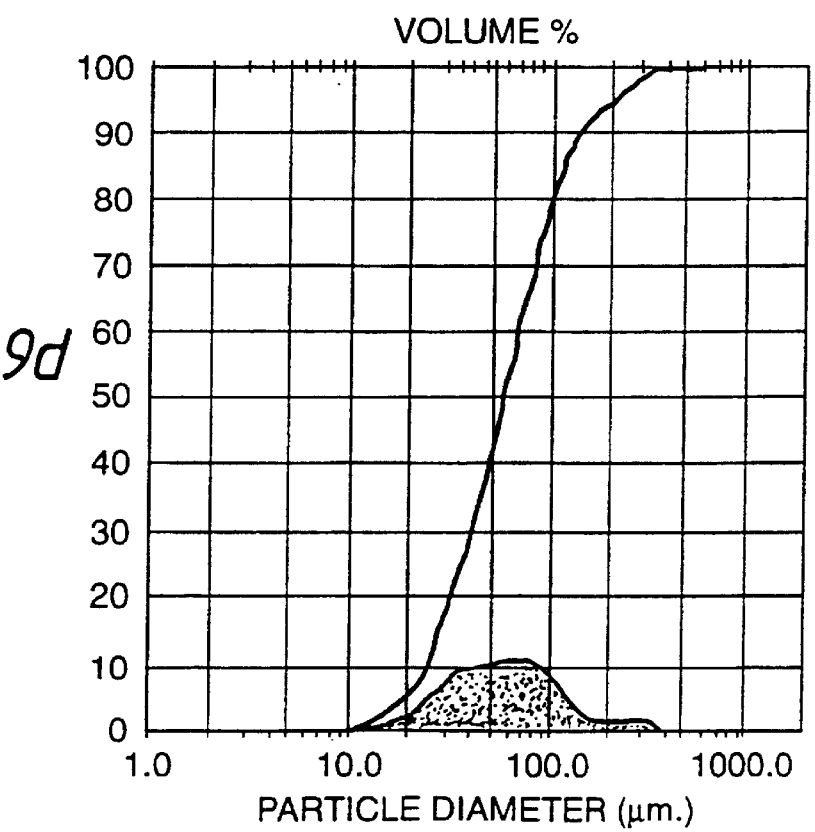

In use, satellite droplets are sometimes produced during the electrohydrodynamic comminution. These satellite droplets will not generally present a problem and will normally deposit onto the interior surface of the inhaler or the second or counter electrode. However, if the inhalers described above are used frequently over an extended period of time, the build-up of droplets and/or residue resulting from subsequent evaporation of the droplets may adversely affect the operation of the counter electrode 12 so reducing the overall efficiency of the device. One way to avoid this problem is to design the inhaler body so that, for example, the portion 4*a* of the housing defining the chamber 1*b* can be removed (for example the housing portion 4*a* may be connected by screw-thread connected to the housing portion 4*b*) to enable a user to wipe the counter electrode to remove deposited droplets or other matter. An alternative, automatic means of maintaining the operational function of electrode 12 is described below.

FIG. 6 shows a part-cross-sectional view of mainly the lower chamber 16 of another inhaler embodying the invention. The internal construction of the upper chamber 1*a* is essentially the same as that described above with reference to FIG. 2.

In FIG. 6, the counter electrode 12' is mounted to the inner wall 1*b* of the lower chamber 1*b*. The counter electrode 12' may be annular or may be formed by a discrete single point electrode or a number of separate electrically connected electrodes spaced apart around the wall 1*b*'.

The counter electrode 12' is, in this example, an uncoated electrically conductive electrode which is coupled via wire 50' and a resistor R to the conductor 5' which is coupled to the negative or earth terminal of the voltage source 5.

A further electrode 120 is mounted in a conventional manner (not shown) in the lower housing 1*b* so as to be considerably closer to the counter or second electrode 12 than to the first electrode 11. Typically, for the dimensions given above for the inhaler, the electrode 120 may be 2 mm from the counter electrode 12' and 5 mm from the first electrode 11. The counter electrode 120 is coupled via the conductor 7*a* to the high voltage output of the high voltage generator 7 (not shown in FIG. 6).

When an inhaler having the structure shown in FIG. 6 is used, the high voltage applied to the electrode 120 causes ions to be generated by corona discharge from the electrode 120. These ions migrate to the closest conductive body—in this case the counter electrode 12'—so providing an ion current to earth via the counter electrode 12' and the resistor R which may, typically, have a value of 600 megaohms. This enables the counter electrode 12' to be indirectly charged to the required electrical potential. Any charged comminuted matter issuing from the nozzle 10*a* which is inadvertently attracted toward the counter electrode 12' will be at least partially electrically discharged by the ion current generated by the ion generating electrode 120 so reducing the likelihood of the charged matter depositing onto the counter electrode 12' and obviating the need for a user to wipe the counter electrode periodically.

FIG. 7 illustrates a modification of the arrangement shown in FIG. 6 in which the resistance provided by the coating of the counter electrode 12" is sufficient to enable the required electrical potential to be achieved at the counter electrode 12" without the need for the resistor R. In other respects, the arrangement shown in FIG. 7 operates in the same manner as the arrangement shown in FIG. 6.

Although FIGS. 6 and 7 show only one ion generating electrode 120, a plurality of ion generating electrodes 120 may be provided around the liquid supply pipe. As another possibility, the ion generating electrode may be provided by a knife edge or wire surrounding the liquid supply pipe.

It has been found that the arrangements shown in FIGS. 6 and 7 enable a more even distribution of comminuted matter to a greater depth within the nasal passages; thus improving the uniformity of droplet distribution still further. This is believed to arise because electrically charged comminuted matter which comes into the vicinity of the ion injecting electrode 120 will have been at least partially electrically discharged so that some of the comminuted matter which is inhaled will be less highly charged and will therefore have a tendency to be deposited further into the nasal passages.

The air flow path in FIGS. 6 and 7 may be modified as described above with reference to FIG. 5 to provide the second electrode with a protective air curtain.

In the arrangements described above, the airflow switch SW2 is activated by the user inhaling. It is, however, possible that the user may be so frail that they are not capable of inhaling sufficiently strongly to activate the switch SW2. In such a case, the inhaler may be provided, as shown in FIG. 8, with an adaptor 100 which couples around the area of the switch SW2 and can be connected via a pipe 101 to a manually actuable device 102 such as a bladder or bellows which can be squeezed by the patient or another person such as a doctor, nurse or carer to force a flow of air to open the air inlet 30 and close the switch SW2 or to a pressurised air or gas bottle or a compressor which may be electrically operated to supply air at the desired flow rate down the pipe to the air inlet 30.

FIGS. 9*a* to 9*d* show experimental droplet spectra produced using a Malvern Mastersizer X manufactured by Malvern Instruments of Malvern, UK. FIG. 9*a* shows a typical droplet spectrum produced using a device of the type shown in FIG. 1. As can be seen from FIG. 9*a*, the medium particle or droplet diameter is around 10 $\mu$m which is at the lower end of desirable droplet diameters for nasal delivery. FIGS. 9*b* to 9*d* show the equivalent droplet spectra produced by three commercially available nasal inhalers with FIG. 9*b* showing the droplet spectra produced by an "Otravine" (Registered Trade Mark) nasal inhaler which comprises a squeezable plastic bottle supplying xylometazoline hydrochloride as a nasal decongestant and is supplied by Novartis Consumer Health of Horsham RH12 4AB, UK, FIG. 9*c* showing the droplet spectra for a "Flixonase" nasal inhaler and which uses a metering valve and a pressurised reservoir and which supplies fluticasone propionate and is supplied by Allen & Hanburys of Stockley Park, Middlesex UB11 1BT, UK and FIG. 9d showing the droplet spectrum output by a "Beconase" pump action nasal inhaler which comprises beclomethasone dipropionate and is also supplied by Allen & Hanburys. As can be seen from a comparison of FIGS. 9b to 9d with FIG. 9a, the three conventional inhalers produce a larger range of particle or droplet diameters and control over the droplet sizes is poor in comparison to that achievable with the electrohydrodynamic device shown in FIG. 9a. It should also be noted that the conventional inhalers do not charge the droplets and rely on turbulence and inertia alone to deposit the droplets. Furthermore, the performance of conventional propellant inhalers is very dependent on the air flow in the nasal passages that can be generated by the user.

Figure 1:
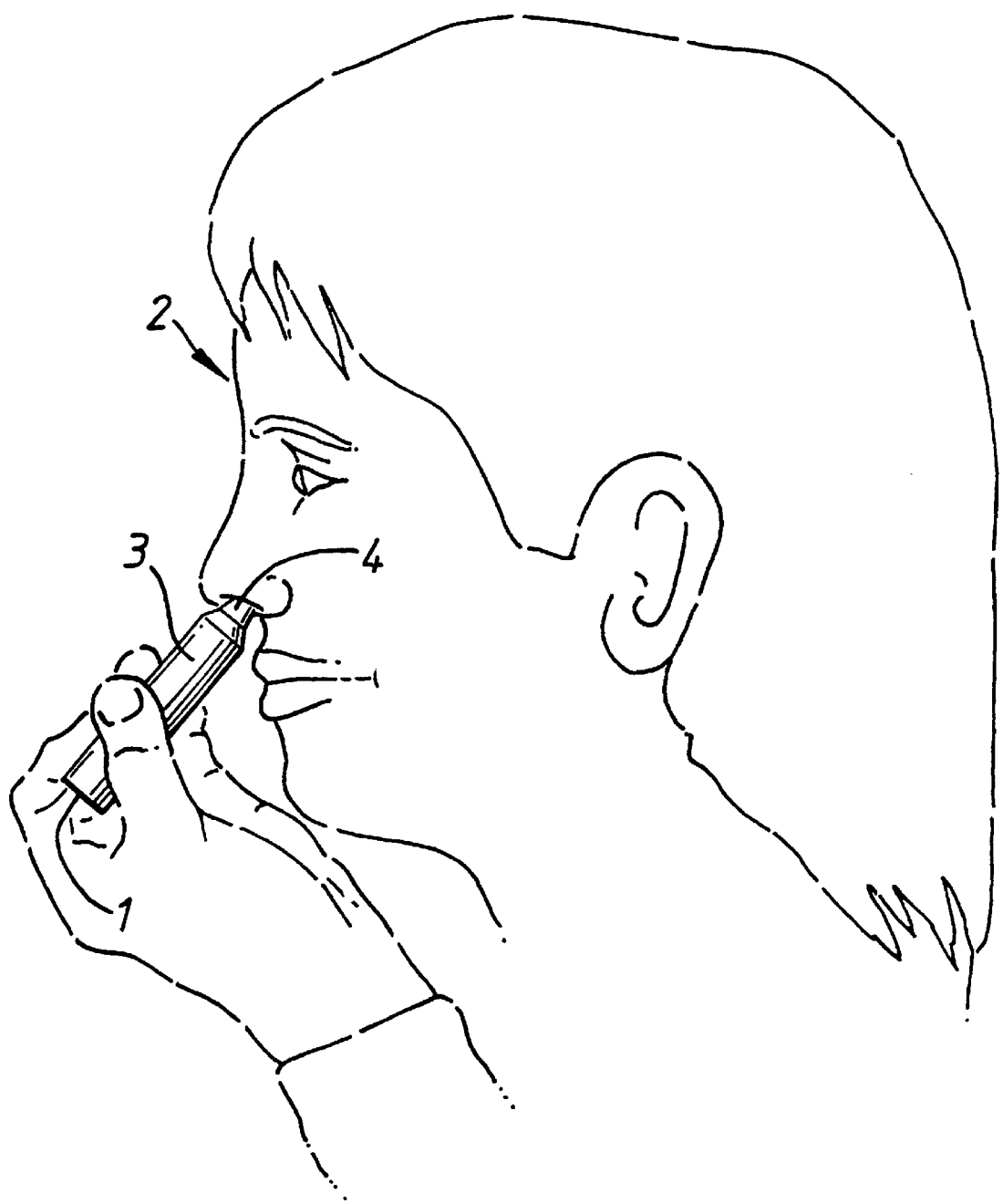

The operation of the inhaler 1 shown in FIG. 1 has been tested on models of the nose and it has been found that the resulting charge sprays deposit evenly over the conductive surface representing the interior of the nose. The liquid used in these experiments had an electrical resistivity of 4500 Ωcm, a surface tension of 30 mN/m (milli Newtons per metre) and a viscosity of 2.4 cP (centipoise) and a voltage in the range of 8 to 12 kV was applied between the first and second electrodes.

Figure 10:
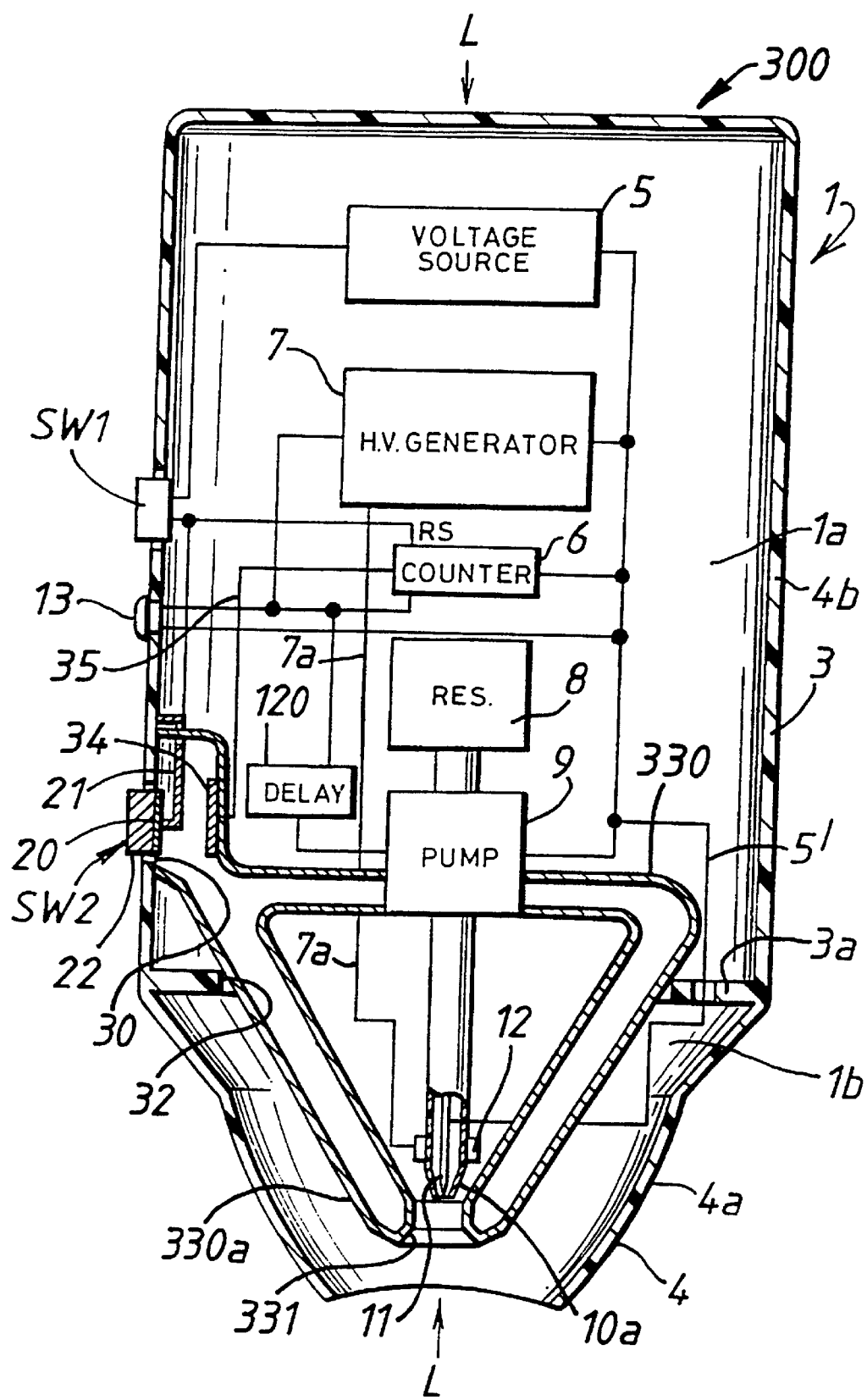

The embodiments described above are intended primarily for comminuting liquids of relatively high resistivity such as oils and alcohol. FIG. 10 shows a modified version of the inhaler shown in FIG. 2 that is suitable for comminuting very electrically conductive liquids such as water and salt solutions.

Figure 2:
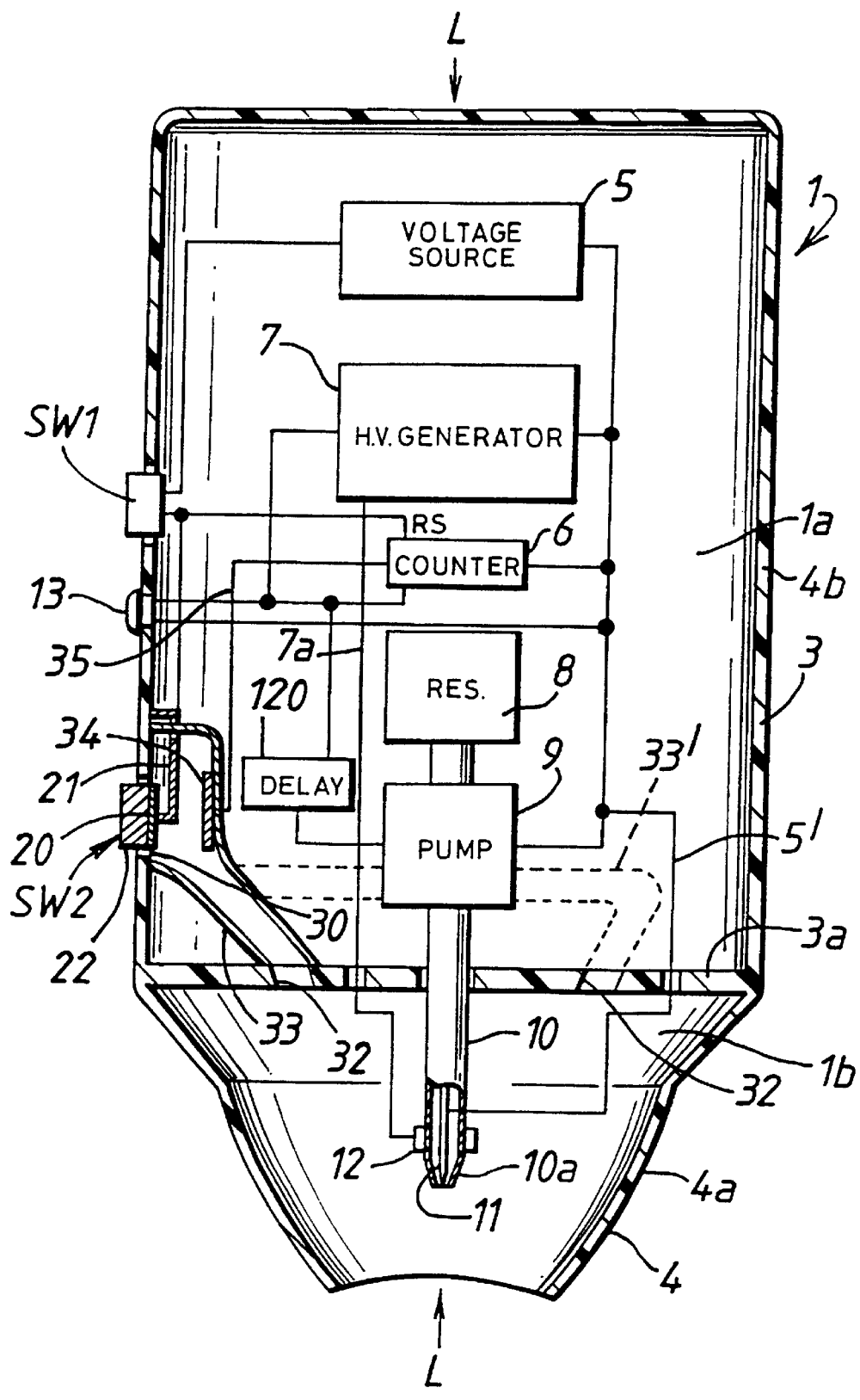

In the inhaler 300 shown in FIG. 10, the air path tube 33 shown in FIG. 2 is replaced by an air path tube 330 in the form of a hollow body defining an air channel 330a which extends through an aperture 32 in the wall 3a to terminate in a ring-like nozzle outlet 331 surrounding the outlet nozzle 10a. In all other respects, the inhaler 300 shown in FIG. 10 is the same as that shown in FIG. 2.

The inhaler 300 operates in the same way as the inhaler 3 shown in FIG. 2 apart from one significant aspect. Thus, when a user takes a sharp intake of breath through a nostril using the inhaler 300, a fast moving stream of air is supplied via the nozzle 331 to the area in which comminution occurs. The air flow from the nozzle 331 acts to shear droplets that are electrohydrodynamically formed from liquid issuing from the outlet nozzle 10a so resulting in droplets that are smaller than they would be without the air flow. This enables the inhaler to be used for conductive liquids such as water and salt solutions which are otherwise difficult to comminute electrohydrodynamically.

Experiments have been carried out using tap water as the liquid to be comminuted with a liquid supply pipe having an outlet nozzle 10a with an internal diameter of 0.2 mm and with 2.5 kilovolts applied between the first and second electrodes 11 and 12. The diameter of the tube is selected in accordance with the average expected nasal inhalation rate of a user to provide an air flow rate from the nozzle 331 sufficient to cause shearing, in this example 10 m/second. Where the air flows at approximately 20 to 30 litres/minute through a tube which is coaxial with and surrounding the outlet nozzle, then generally the tube outlet should have an area of a few square millimetres so as to be comparable with the air flow impedance provided by the nasal passages.

Droplets having a diameter of approximately 20 micrometers were detected. The droplet charge to mass ratio was determined to be approximately $10^{-4}$ coulombs/kilogram. The droplets were thus significantly smaller than they would have been without the air flow.

The air flow rate of approximately 10 m/second mentioned above is sufficient to cause shearing and is roughly equivalent to the air flow generated by a relatively healthy person taking a sharp intake of breath.

It will be appreciated that the modification described with reference to FIG. 10 may be used in combination with any appropriate ones of the modifications described with reference to any one of FIGS. 4 to 8 above so that, for example, the counter electrode 12 may be positioned downstream of the first electrode 11 as shown in FIG. 5. It will also be appreciated that one, two or more air flow nozzles may be provided in the vicinity of the comminution area or site. All that matters is that a sufficient air flow is achieved at the comminution area or site to cause shearing without causing undue turbulence. In this regard, it will be noted that as shown in FIG. 10, the outlet nozzle 331 is directed so as to provide an air flow extending obliquely of the direction in which liquid issues from the outlet nozzle 10a.

Apart from the reasons given in the introduction of this application, a person skilled in the art may have thought that it would be undesirable for the user of an inhaler to inhale charged droplets because the supply of charge to the user would, if the user was not earthed during use of the inhaler, result in a voltage rise of the user which could result in the user experiencing an unpleasant electrical shock when he subsequently was connected to earth.

The present inventors have, however, found that the rise in the voltage of an unearthed user during a single use of an inhaler embodying the invention is not sufficiently large to result in an unpleasant electrical discharge. Also, the amount of charge transferred to the user may, if desired, be controlled to a minimum. This may be achieved by, for example, formulating the liquid carrying the medicament being inhaled with a higher concentration of the active ingredient or medicament in the liquid than is normal with aqueous solutions. Thus a smaller amount of liquid need be inhaled to deliver the required dose. This reduces the overall space charge and facilitates entrainment of the comminuted matter in the air flow through the inhaler. Typically, the concentration may be increased by five fold (say from 10% to 50% by volume of the active ingredient).

If prolonged or continuous treatment is required, then the inhalers described above may be modified to periodically reverse the polarity of the voltage supplied by the high voltage generator so that the user receives droplets of one polarity charge followed by droplets of the opposite polarity charge, thereby inhibiting any significant rise in the voltage of the user. One simple way in which this may be achieved is to use as the high voltage source a piezoelectric generator which is manually activated by the user using a cam and lever arrangement because this automatically provides a polarity reversal with the voltage generated when the crystal is squeezed being of opposite polarity to the voltage generated when the crystal is released.

In each of the examples described above, the high voltage is applied to the second or counter electrode. However, the second electrode could be omitted and the first electrode charged directly to the required high voltage, especially if a low power, low capacitance, high voltage generator, such as a piezoelectric generator, is used.

Figure 11:
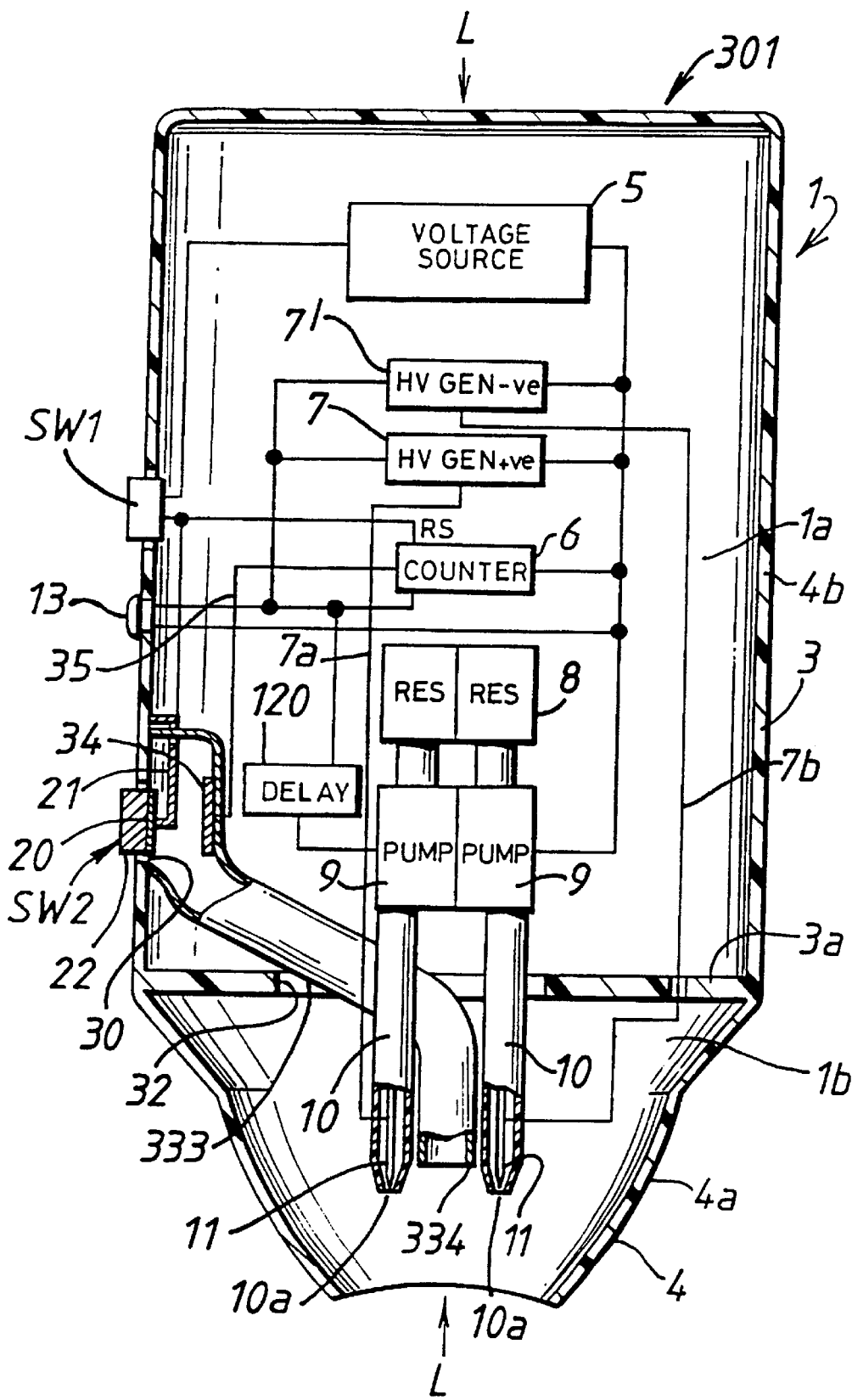

FIG. 11 shows a diagrammatic part-cross-sectional view similar to FIG. 2 of another embodiment of an inhaler in accordance with the present invention where the first electrode is directly charged.

The inhaler 301 shown in FIG. 11 has two liquid supply pipes 10 each having an outlet nozzle 10a. The pipe 10 is coupled to a corresponding pump 9 so as to receive liquid from a corresponding reservoir 8. Although not shown explicitly in FIG. 11, each pump 9 is coupled between the delay circuit 120 and the negative terminal of the voltage source 5. Each of the liquid supply pipes 10 has supported within it a first electrode 11 in the form of a conductive core. The first electrode 11 of one liquid supply pipe 10 is coupled to the high voltage output of the high voltage generator 7 (not shown in FIG. 6). A further high voltage generator 7' providing a high voltage of the opposite polarity, negative in this case, has its high voltage output coupled to the first electrode 11 of the other liquid supply pipe 10. In this case, either the liquid should be sufficiently highly resistive to inhibit the direct charging of the first electrodes 11 causing a voltage rise at the pump or the pump should be electrically isolated from the liquid.

The air flow path shown in FIG. 11 is also different from that shown in FIG. 2. Thus, in the inhaler 301 shown in FIG. 11, the insulative tubular body 33 of FIG. 2 is replaced by an insulative tubular body 333 which passes through the aperture 32 in the wall 3a so as to terminate at an air outlet nozzle 334 which, as shown in FIG. 11, is coaxial with and symmetrically disposed between the two liquid outlet nozzles 10a. The inhaler 301 shown in FIG. 11 operates in a similar manner to the inhaler shown in FIG. 2 with the exception that two opposite polarity sprays or comminutions are produced. The air flow from the air outlet nozzle 334 is sufficient to keep the two opposite polarity comminutions apart so that two opposite polarity comminutions are supplied to the nozzle passages. This has the advantage of enabling charged, comminuted matter to be supplied to the nasal passages without altering the overall charge of the body of the user. Typically, the longitudinal axes of the two liquid supply pipes may be 12 to 15 mm apart.

It should be appreciated that the modifications described with reference to FIG. 11 may be used in combination with the modifications described with reference to any one of FIGS. 4 to 8 above.

Figure 8:
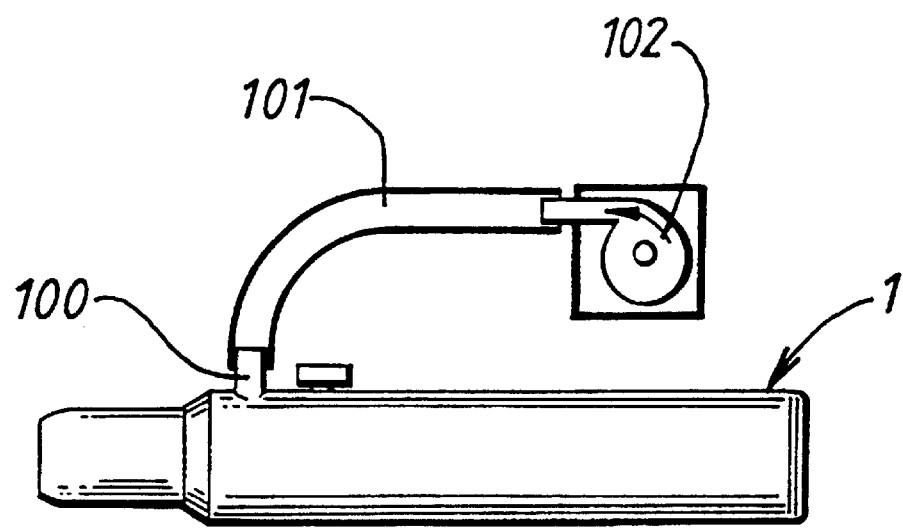
Figure 12:
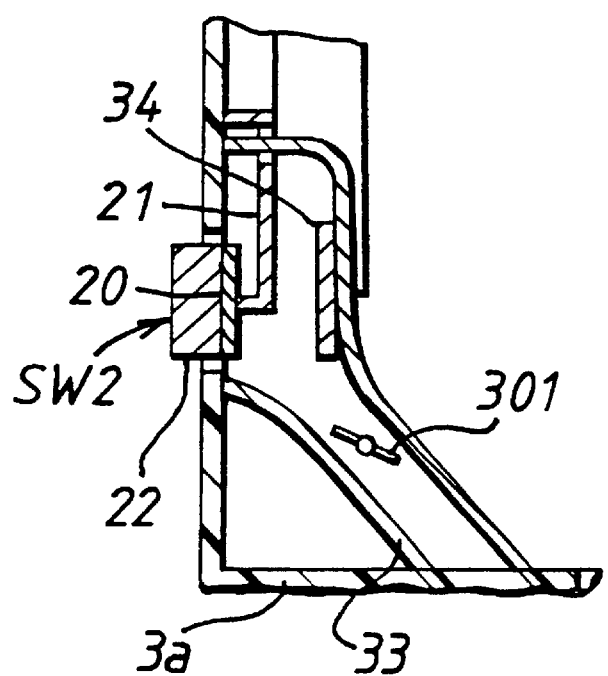

In each of the embodiments described above the air flow rate is controlled either by how hard the user sniffs or by, in the case of FIG. 8, the operation of the pump 102. Further control of the air flow rate in any of the above described embodiments may be provided by means of a valve in the air flow path. As an example, FIG. 12 shows part of the inhaler shown in FIG. 2 with a flap valve or choke 301 pivotally mounted in the air flow path 33. The flap valve may be operable by means of any conventional mechanism, for example, the flap valve may be manually rotatable by a user rotating a knob mounted to the outside of the housing or pivoting movement of the flap valve may be controlled mechanically using a camming arrangement or electromechanically using a camming arrangement and a solenoid, for example, or may be arranged to be present by a doctor, for example. Other conventional forms of valves may also be used.

As described above, the air flow from the outlet nozzle 334 serves to keep the opposite polarity sprays or comminutions apart. The amount by which the opposite polarity comminutions are kept apart, and so a degree of mixing can be controlled by controlling the air flow rate through the pipe 334 by, for example, providing a throttle or like valve in the air flow pipe 334. This air flow valve may be preset by the doctor or at factory level (for example in dependence upon the active ingredient to be delivered by the inhaler), or may be settable by the user. The zone of deposition of the comminuted matter in the nasal passages can be controlled by controlling the overall charge of the comminuted matter supplied to the nostrils of the user so enabling the area to which the active ingredient is to be delivered to be targeted by adjusting the air flow rate with an air flow control valve.

It will be appreciated that different users or different patients may have different nasal inhalation rates which, with conventional propellant nasal inhalers, would cause the inhaled material to be deposited more deeply into the nasal passages than if the inhaler was being used by a person with a lower nasal inhalation rate. However, the nasal inhaler shown in FIG. 11 has the advantage that a person with a rapid nasal inhalation rate will cause a more rapid flow of air from the air outlet nozzle 334 than will a person with a low nasal inhalation rate so that the person with the high nasal inhalation rate will receive more highly charged, less mixed, comminuted matter than the person with the low nasal inhalation rate. As more highly charged matter tends to penetrate less deeply into the nasal passages, the inhaler shown in FIG. 11 provides a self-adjusting effect because the tendency of a greater inhalation rate to cause material to be deposited more deeply into the nasal passages is counteracted by the greater charge tending to cause the material to be deposited less deeply into the nasal passages.

In the arrangement shown in FIG. 11, the liquid outlets 10a are parallel to one another. However, the liquid outlets may be angled towards one another, for example at 45° to the longitudinal axis L of the inhaler, which may increase the degree of mixing.

The overall charge on the comminuted matter delivered by the inhaler and thus the depth to which that matter penetrates into the nasal passages may also be controlled by, in addition to or instead of controlling the air flow rate, controlling the relative voltages applied to the two first electrodes by adjusting the voltages supplied by the high voltage generators 7 and 7' and/or by adjusting the relative flow rates of liquid to the outlet nozzles 10a. These adjustments may be adjustments that can be made at factory level so that a single inhaler construction can be adapted within the factory for delivery of different doses (for example for children and adults) of the same active ingredient or to enable the same inhaler to be used to deliver different active ingredients which require different dosages. As another possibility, the voltages supplied by the generators and/or the flow rates may be adjustable by a doctor or nurse under clinical conditions or a pharmacist or the patient or user himself where it is acceptable for the user to control the dose supplied.

As described above, it is assumed that the same liquid is supplied to the two liquid supply pipes 10. If this is the case and relative flow rate adjustment is not required, then a single reservoir 8 and a single pump 9 may be provided. Also, instead of providing separate negative and positive polarity high voltage generators, a single generator providing a high voltage of one polarity to one of the first electrodes 11 may be provided and the other electrode may be connected to earth (ground) so that, in practice, it is charged by induction from the directly charged first electrode. This has the advantage of requiring only a single high voltage generator so reducing the overall costs and reducing the space required within the inhaler to accommodate the high voltage generator.

Where, as shown in FIG. 11, respective reservoirs and pumps 8 and 9 are provided, then the two liquid supply pipes 10 may be supplied with different liquids that, when the opposite polarity comminutions are generated, interact with one another. For example, the two liquids may contain or comprise respective reactive components that, when the two opposite polarity comminutions are produced, intermingle and react with one another so as to produce the required active ingredient. This enables, for example, short shelf life active ingredients to be formed only as and when needed. As another possibility, the two liquid supply paths may provide separate active ingredients for which reaction is not desirable but which lose their relative efficacy if they are in the presence of one another for any length of time. As another possibility, one of the liquids may contain a blowing agent which, when comminuted matter contained in the blowing agent reacts with the opposite polarity comminuted matter, causes expansion of the droplets or particles of the other comminuted matter to form low density particles, for example spheres, which can penetrate deeper into the nasal passages. As another possibility, where the liquid issuing from one of the outlets produces comminuted matter in liquid or gel-like form, then, when the two opposite polarity comminutions mix, the liquid or gel-like comminuted matter may cover or coat particles of the other comminuted matter to form, for example, microcapsules or coated short fibres or fibrils enabling slow release of active ingredient from the cores of the coated particles. The coating material may contain a bioadhesive to prevent mucocillary clearance and to facilitate long term or sustained release of the active ingredient when used in conjunction with controlled release products.

Another advantage of having two liquid outlets is that the overall rate at which the active ingredient is delivered to the nasal passages should be higher than if only a single liquid outlet nozzle is used. It will be appreciated that more than one pair of liquid outlets may be used and that it is not necessary for there to be equal numbers of positive and negative charged first electrodes especially where, if the arrangement allows complete mixing of the comminutions, a residual charge should be ensured.

Another advantage of providing plural nozzles to achieve opposite polarity comminutions is that the comminution sprays will be more strongly attracted to one another than to the walls of the housing and so the possibility of deposition of comminuted matter onto the walls of the housing should be reduced.

Also, the arrangement shown in FIG. 11 should enable larger size droplets or particles of comminuted matter to be produced carrying a given charge.

It will be appreciated that, although the counter electrodes 12 are not necessary in the arrangement shown in FIG. 11, the arrangement shown in FIG. 11 could be adapted to provide counter electrodes in a similar manner to that described above with reference to FIG. 2 with the respective counter electrodes being coupled to the respective negative and high voltage generators 7 and 7' and the first electrodes 10 being coupled to the negative terminal of the voltage source or to the high voltage generator of opposite polarity It should also be appreciated that the counter electrodes need not be coated with a dielectric although this is often preferable. This arrangement may facilitate use of the inhaler shown in FIG. 11 with more conductive liquids.

In the arrangement shown in FIG. 11, the air supply outlet 334 is disposed centrally of the two liquid outlets. Although this is preferable where it is desired to keep the two opposite polarity comminutions apart, where at least some mixing is desired, then the air outlet may surround the liquid outlets and, for example, air inlet apertures may be provided in the housing wall 4a. Providing the air outlets around the liquid outlets should, in addition to facilitating desired mixing, provide an air curtain to inhibit or at least reduce further the possibility of deposition on the walls of the housing.

As discussed in WO98/03267, in electrohydrodynamic comminution, the intense electric field to which liquids issuing from the nozzle outlet 10a is subject establishes a standing wave along the surface of the liquid producing at least one cusp or cone (depending upon the size of the outlet 10a) which emits a jet or jets of charged liquid. Small perturbations inevitably occur in the liquid jet resulting in a growth wave which causes the jet to become unstable and the net electrical charge in the liquid provides a repulsive force which counteracts the surface tension forces in the liquid to cause comminution. The growth wave will have a natural frequency and it has been found that the point at which initiation of the growth wave occurs in the jet can be controlled by superimposing upon the applied high voltage an AC signal different from the natural frequency of the growth wave enabling the size of the resulting droplets to be controlled.

The present inventors have found that, instead of a monodispersed comminution, a comminution having droplets of two or more well-defined controlled diameters can be produced by superimposing on the high voltage signal an oscillating signal comprising one or more superimposed frequencies close to natural frequency of the growth wave for the liquid being comminuted.

As shown schematically in FIG. 13, a pulse or signal generator 70 is coupled to the high voltage supply line 7a of the high voltage generator by means of a high voltage capacitor C. However, it might be possible to use the natural frequency of the high voltage generator 7 and to retain some AC ripple on the H.V. output line 7a.

Any suitable form of pulse or signal generator which may be powered by the voltage source 5 (see FIG. 2 for example) of the inhaler may be used. For example, the pulse/signal generator 70 may comprise a number of voltage controlled oscillators each of which receives a respective different drive voltage derived in known manner using voltage dividing or multiplying techniques from the voltage source. As another possibility, a numerically controlled oscillator may be used. For example, the pulse/signal generator may comprise a digital memory storing at sequential addresses numerical values which are read out in sequence from the memory and supplied to a digital-to-analogue converter to reconstitute the desired wave shape. In such a case, a signal representing the superimposition of two or more frequencies may be directly generated from the numbers stored in the memory. Reference may be made to standard electronics textbooks such as 'The Art of Electronics' by Paul Horowitz and Winfield Hill for details of oscillators which may be used to provide the pulse/signal generator 70.

FIG. 14 illustrates how a superimposed varying amplitude voltage can affect droplet formation with large and small amplitude impulses or "kicks" (illustrated schematically by line 71) applied to the H.V. output line giving rise to two different size droplets d and D.

When the inhaler shown in FIG. 2 is modified in this manner, in use, liquid issuing from the outlet nozzle 10a is electrohydrodynamically comminuted and is deposited on the conductive surface inside the nostril as the user inhales as described above. However, the smaller droplets which carry less charge and have lower inertia will travel further into the nasal passages than the larger droplets so enabling a more uniform deposition along the length of the nasal passages of the medicament being delivered.

It will be appreciated that superimposing three or more frequencies will allow three or more different size droplets to be produced in a controlled manner.

Instead of superimposing the different frequencies, different frequency signals may be supplied in sequence to the high voltage line 7a so that the size of the droplets produced changes in a controlled manner with time depending upon the particular drive frequency applied at the time the droplets are generated.

The arrangement discussed above with reference to FIGS. 13 and 14 assumes that the drive signals are sine waves. However, this need not necessarily be the case and, for example, short duration spikes having a pulse width of 1 microsecond or less may be used. Typically the drive signals provided by the pulse generator 70 will have an amplitude of about 2% of the high voltage, for example 10–100 volts and a frequency in the range of 50 kHz to 10–50 MHz, depending upon the desired size of the droplets.

Another possible form of oscillation device is a piezo-electric resonator with two or more resonators arranged to resonate at different frequencies being provided to achieve the required drive frequencies.

Figure 15:
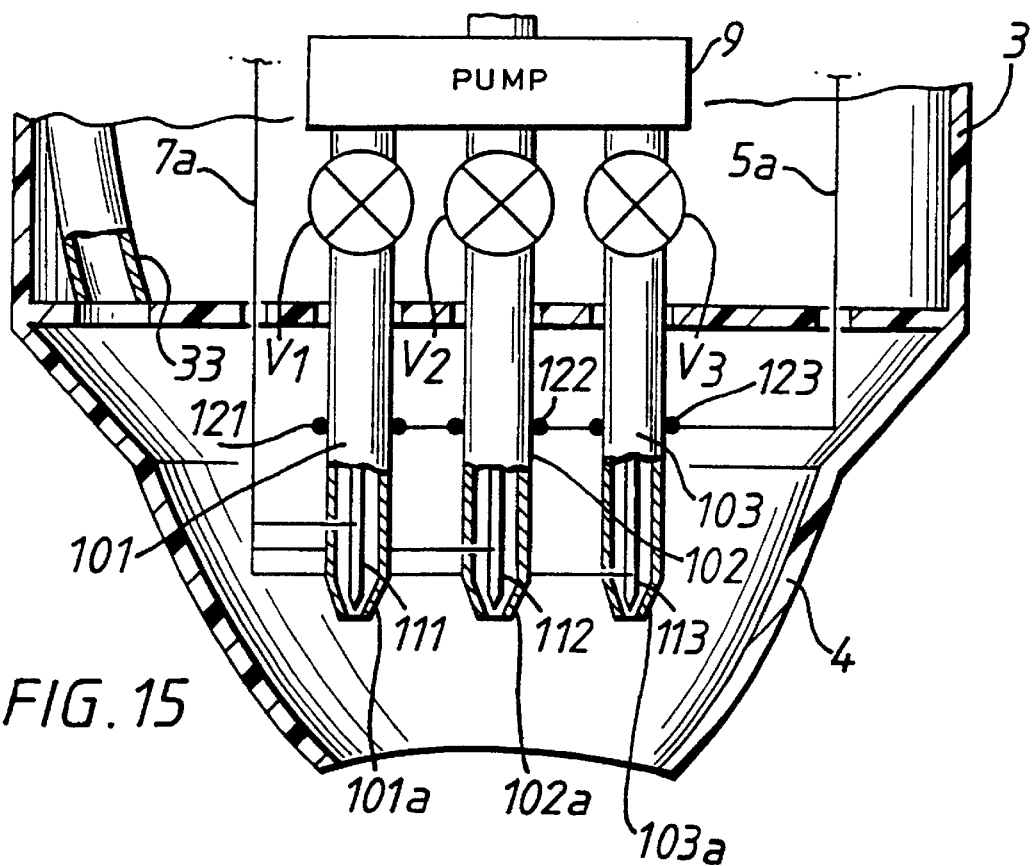
Figure 16:
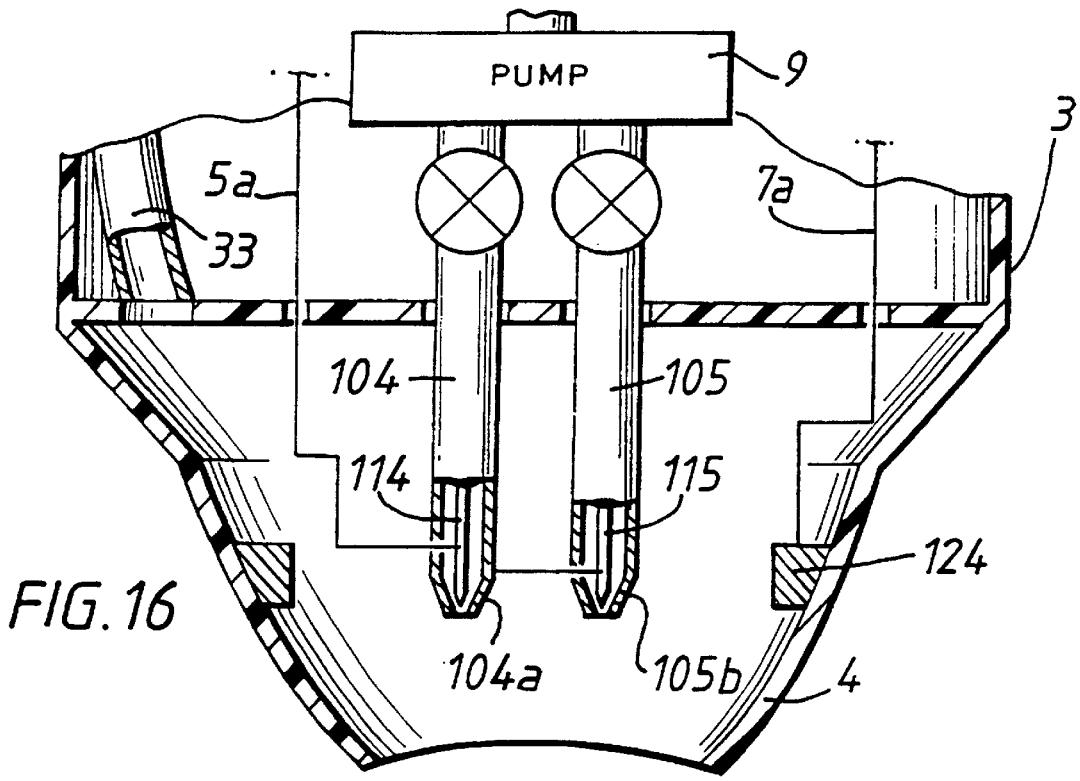

FIGS. 15 and 16 show schematically parts of further modified versions of the inhaler shown in FIG. 2.

In the arrangement shown in FIG. 15, the pump 9 is arranged to supply liquid to three liquid supply pipes 101, 102 and 103 each having a corresponding outlet 101a, 102a and 103a and each containing a conductive core or rod 111, 112 and 113. The conductive core or rod in each case is coupled to the earth terminal of the voltage generator 5 via line 5a while a second electrode 121, 122 and 123 carried by the insulative supply pipe 101, 102 and 103 is coupled to the high voltage output line 7a from the high voltage generator. Each of the supply pipes 101 to 103 has a flow regulating valve V1, V2 and V3. Each flow regulating valve V1, V2 and V3 controls the rate of flow of liquid through its associated liquid supply pipe so that the rate of flow of liquid from each of the outlets 101a, 102a and 103a is different. Any suitable form of valve, for example a simple mechanical throttle valve or an electromechanical solenoid valve, may be used. Because the flow rates to the respective outlets 101a, 102a and 103a are different, the size of the droplets produced during electrohydrodynamic comminution from the respective outlets will be different. Accordingly, the embodiment shown in FIG. 15 enables three different sizes of droplets to be produced by providing respective different flow rates for the three liquid supply pipes.

It will be appreciated that two, three or more liquid supply pipes having different liquid flow rates may be used and that the liquid flow rates may be prefixed or may be adjustable by the user. The embodiment shown in FIG. 15 enables simultaneous production of different size droplets. Sequential production of different size droplets may be achieved by having a single liquid supply pipe and adjusting the flow rate with time by controlling the degree to which the liquid supply valve is open.

FIG. 16 illustrates another modification. In this case, the pump 9 is provided with two or more liquid supply pipes 104 and 105 each having a central conductor or rod 114 and 115 providing a first electrode. In this case the second electrode 124 is mounted to the housing 4 wall. In this case, the liquid supply pipes 104 and 105 are of different cross-sections and therefore provide different liquid flow rates.

As another alternative, different pumps providing different flow rates may be used for the different liquid supply pipes.

The generation of comminutions at the different outlets in FIGS. 15 and 16 may be synchronised by superimposing upon the high voltage signal on line 7a a drive signal comparable to the natural frequency of the growth rate using the pulse generator 70.

In each of the embodiments described above, an air flow is generated within the lower portion 4a of the housing. In order to avoid air movements disrupting the Taylor cone required at the liquid outlets for electrohydrodynamic comminution, an annular shield may be provided around the liquid pipes in the immediate vicinity of the liquid outlets 10a.

Figure 3:
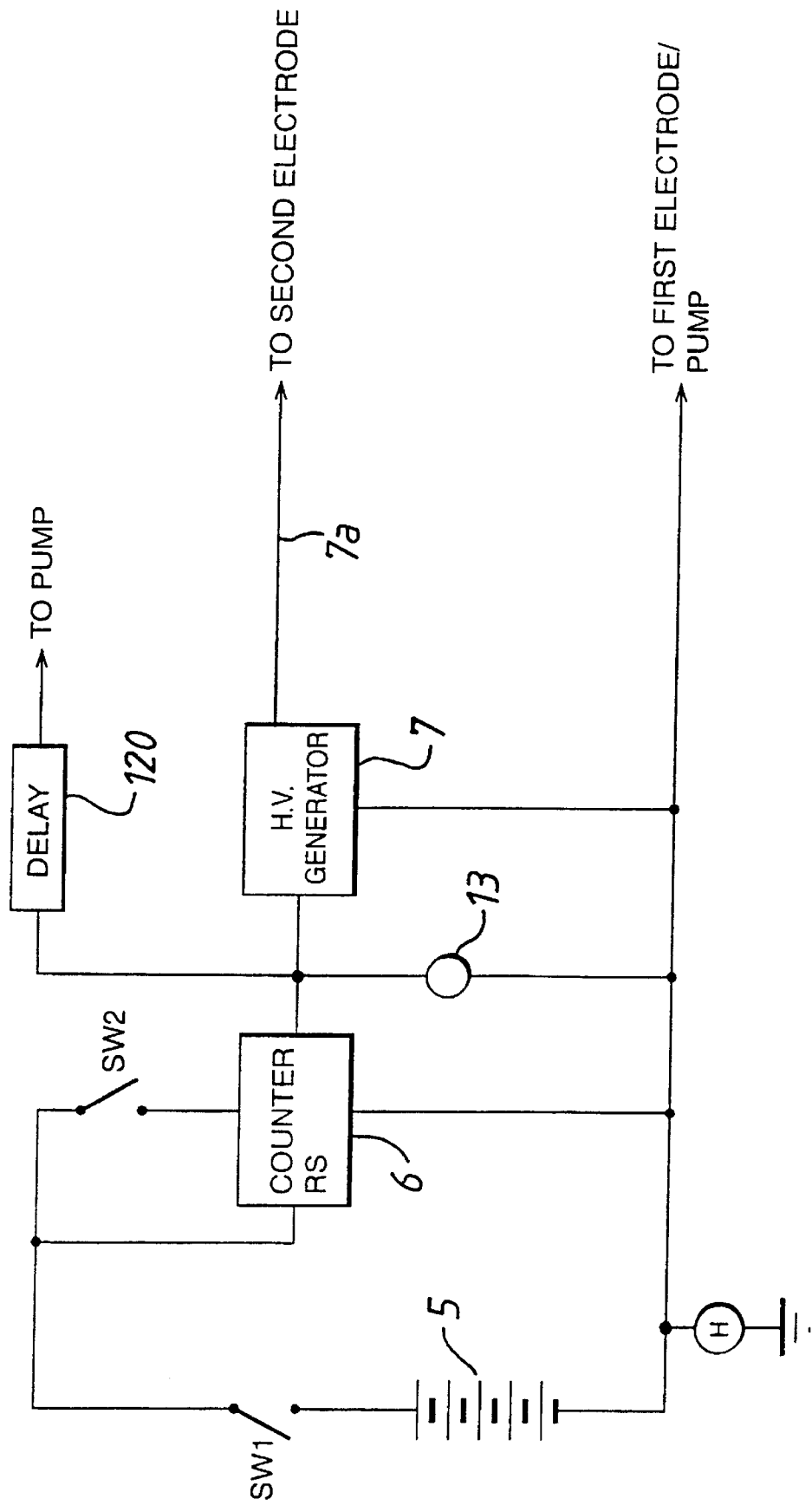

In each of the embodiments described above, the inhaler is designed to enable multiple doses to be supplied from a single reservoir or reservoirs 8. The inhaler 1 may, however, be a single dose inhaler with a reservoir containing only sufficient liquid formulation to provide a single dose. Where this is the case, then the counter 6 and LED 13 described above with reference to FIG. 3 may be omitted. In the case of a single dose inhaler, the liquid supply components may be provided as a replaceable plug-in cartridge that can be replaced by the user. Where this is the case, then for ease of manufacture and because these components are relatively cheap, the liquid cartridge will generally include the first electrodes 11, and the electrodes 12 if present and if not carried by the housing portion 4a. As another possibility, the inhaler may be provided with a carousel or magazine of capsules which carousel or magazine is capable of indexed movement so that, after each use of the inhaler, a fresh capsule is moved into place for the next use. Such a magazine may be in the form of a strip carrying the capsules which is, for example, wound from one spool to another as the capsules are used up.

In the embodiments described above, the inhaler has a single outlet for a single nostril. The inhaler may be provided with twin outlets, one for each nostril.

Although particular forms of electrohydrodynamic comminution means have been described in the examples given above, it will be appreciated that other forms of electrohydrodynamic comminution means can be used. Also, other forms of electrically operable pump may be used.

Electrically or electromechanically operated valves may be provided at appropriate points in the liquid flow path from the reservoir to the outlet 10a so as to inhibit leakage and maintain microbial integrity.

Although the above arrangements are described with reference to the supply of an active ingredient to a human being (solely by the user or with the assistance of a doctor, nurse or carer), it will, of course, be appreciated that the device may be adapted for use with other mammals with the air flow activation being controlled as described with reference to FIG. 8 by a veterinarian or other person.

The active ingredient to be supplied by the inhaler may be any agent or substance to provide a desired effect in the user. For example, the active ingredient may be a medicament for use in the treatment by way of therapy, surgery or diagnosis of an animal body such as a human being or otherwise to improve quality of life. For example, the medicament may be nicotine, morphine, a vitamin, an antiseptic, an anti-inflammatory, antibiotic, anti-cancer agent or other pharmaceutical product, a vaccine, a protein, an enzyme, DNA or DNA fragments and so on because electrohydrodynamic comminution enables delivery of large molecules without denaturing them.

The liquid formulation within which the active ingredient is supplied may be a solution, emulsion, suspension or microsuspension or any other suitable liquid form. Because viscous liquids (including oils) such as glycerine and linoleic acid can be comminuted using electrohydrodynamic comminution, the carrier liquid can be optimised for the active ingredient so that, for example, where the active ingredient is a lipophilic compound as may be the case for a drug or medicament, then the use of electrohydrodynamic comminution should simplify the preparation of the formulation for that active ingredient. Also, the use of oils and emollients has the advantages that oil-based medicaments permeate cell membranes better allowing more rapid absorption of the medicament when inhaled into the nasal passages. Also, oils and oil-based formulations should cause less irritation to the nasal passages than alcohol formulations or aqueous salts. Also oils and other low conductivity liquids produce droplets with a low charge to mass ratio so that the charge spray expands at a lower rate, reducing the likelihood of internal deposition within the device. Furthermore, such low conductivity liquids are also less likely, because they are more highly resistive, to initiate short circuits.

As is known in the art, it is extremely difficult to comminute highly electrically conductive liquids satisfactorily using electrohydrodynamic comminution without the use of surfactants which may irritate the nasal passages and so are undesirable for nasal inhalation. The use of relatively highly conductive liquid formulations may, however, be unavoidable. For example, it may be that the amount or type of active ingredient required renders the liquid formulation highly conductive and/or the carrier liquid required, for example water or a water/ethanol mixture containing ionic components, renders the liquid highly conductive. The present inventors have, surprisingly, found that it is possible to obtain satisfactory electrohydrodynamic comminution of such relatively highly conductive liquids without the use of surfactants by incorporating an additional component into the liquid formulation in the form of a medium to high molecular weight polymer. This polymer may be a synthetic or naturally occurring polymer and the molecular weight may, typically, be in the range 40,000 to 400,000.

Experiments have been carried out using a liquid formulation consisting of 70% ethanol and 30% 0.5 mol water Nacl solution (salt water) to mimic a liquid formulation carrying an active ingredient.

A first set of experiments was carried out using PVA (polyvinyl alcohol) as the polymer. For this polymer, a molecular weight of 125,000 was chosen for the experiment. Details of these experiments are set out in table 1 below. The maximum stable flow rate was 3 microlitres/second (ml/s) per nozzle.

TABLE 1

| Example | Formulation | Resistivity/ Ωm | Viscosity/ cP |
|---|---|---|---|
| 1 | 0.1 g PVA in 10 ml liquid formulation | 5.54 | 10 |
| 2 | 0.2 g PVA in 10 ml liquid formulation | 4.20 | 24 |
| 3 | 0.3 g PVA in 10 ml liquid formulation | 4.80 | 72 |
| 4 | 0.4 g PVA in 10 ml liquid formulation | 5.21 | 110 |
| 5 | 0.5 g PVA in 10 ml liquid formulation | 5.10 | 200 |
| 6 | 0.6 g PVA in 10 ml liquid formulation | 5.21 | 360 |
| 7 | 0.7 g PVA in 10 ml liquid formulation | 5.25 | 700 |

In each of examples 1 to 7 satisfactory electrohydrodynamic comminution was achieved. Microscope photographs of the resultant comminutions were taken and it was found that, surprisingly, the geometry or structure of the comminuted matter varied with the amount of polymer added to the formulation. Thus, when the amount of polymer was 0.1 g in 10 ml, the resulting comminuted matter was granular in appearance consisting of spheroidal or near-spheroidal particles. When the amount of PVA was increased to 0.2 g, then the comminuted matter was still granular but some of the granules had tails or were attached to fibrils. As the amount of PVA was increased, that is going from example 2 to example 7, the amount of fibril or tail formation increased so that at example 7 the majority of the comminuted matter was formed of small fibres or fibrils.

Similar experiments were also carried out using PVP (polyvinyl pyrrolidone). Table 2 shows the results of experiments carried out using a PVP molecular weight of 360,000 and a maximum flow rate of 1.5 microlitres/second per nozzle.

TABLE 2

| Example | Resistivity/Ωm | Viscosity/ cP | Product |
|---|---|---|---|
| 8 | 0.2 g PVA in 10 ml liquid formulation | 4.74 | 10 |
| 9 | 0.4 g PVA in 10 ml liquid formulation | 4.76 | 60 |
| 10 | 0.6 g PVA in 10 ml liquid formulation | 5.36 | 180 |
| 11 | 0.8 g PVA in 10 ml liquid formulation | 5.20 | 260 |
| 12 | 1.0 g PVA in 10 ml liquid formulation | 5.32 | 480 |
| 13 | 1.2 g PVA in 10 ml liquid formulation | 5.82 | 740 |

Again, in each of examples 8 to 12, satisfactory electrohydrodynamic comminution was achieved. Again, microscope photographs were taken and again the geometry or structure of the comminuted matter was found to change with the amount of polymer added to the liquid formulation. Thus, where the amount of polymer was 0.2 g in 10 ml (millilitres), the comminuted matter was generally granular with few fibrils or tails, with 0.4 g PVP in 10 ml of the liquid formulation more fibrils or tails were seen, while with 0.6 g PVP in 10 ml of the formulation significant numbers of tails and fibrils were seen with few granular components. Thereafter, the number of fibrils and short fibres seen increased. As a result of further experiments carried out, a formulation with 0.5 g of PVP in 10 ml of the liquid formulation was found to produce granular material with a good proportion of tails or fibrils.

It can thus be seen that, surprisingly, controlling the amount of medium to high weight polymer added to the liquid formulation enables the geometry or shape of the comminuted material to be controlled so that the comminuted material can be varied from granular particles to short fibres and fibrils with, in between, the comminuted material consisting of granular matter some of which has short tails or attached fibrils. The ability to control the shape or geometry of the comminuted matter is advantageous because this means that the shape of the comminuted matter can be tailored to the desired usage. Generally, the fibrils or tails were found to be semi-solid and capable of adhering better to surfaces such as the surfaces of the nasal passages and/or to themselves, so reducing the possibility of muco-cillary clearance. Also, being able to control the size of the comminuted matter from very small granular particles having dimensions less than 1 micrometre to short fibres or fibrils enables the rate at which active ingredient is taken up by the mucous membranes to be controlled with very small particles enabling fast uptake and larger particles enabling slower, more sustained release of the active ingredient. Thus, by tailoring the geometry of the comminuted matter, the rate of delivery of the active ingredient can be controlled.

The use of electrohydrodynamic comminution as described above to enable delivery of active ingredients by inhalation through the nasal passages enables the control of the rate and location of uptake of the active ingredient so that, for example, the active ingredient can be delivered rapidly to the brain with low or little systemic uptake which is particularly important where the drug to be delivered may have deleterious systemic side effects.

The above example describes inhalers for supplying an active ingredient via the nasal passages. However, where the modification shown in FIG. 8 is provided so that inhalation by the user is not required, supply of an active ingredient to other body areas, cavities or organs, or onto or into a wound is possible. Such a device may be used for supply of active ingredients to the eye because the electrodes are not exposed so inhibiting the possibility of electrical shock. Where the device is adapted for supply of an active ingredient to the surface of the eye, then the outlet of the housing may, for example, be shaped so as to conform to the eye socket. A device having the structure of an inhaler described above with the adaptation shown in FIG. 8 may be used to supply pre- or post-operative active ingredients, for example, to reduce, especially in the case of the eye, the likelihood of scar tissue forming after surgery; to supply antibiotics, antibacterials, anaesthetics and the like to the surface of the eye or into a bodily orifice; to supply comminuted matter onto an exposed interior surface of the body during surgery for example to supply an adhesive to repair an incision in an arterial wall; or to apply wound dressing or medicaments onto internal or external bodily wounds.

The final form of the comminuted matter will depend upon the liquid being comminuted. Thus, for example, if the liquid is such that it starts to solidify or gel after comminution then solid or gel-like droplets will be formed. If the liquid starts to solidify or gel just before comminution then generally small fibres or fibrils will be formed. Where the device is not being used for inhalation, then the term comminution is also intended to cover the case where the supplied liquid solidifies or gels before the applied electric field can break the liquid apart and so forms a single fibre although, strictly, in this circumstance the liquid is not comminuted because it does not necessarily break up.

Other modifications will be apparent to the person skilled in the art.

What is claimed is:

1. An inhaler, comprising a housing having an outlet and an air inlet, the housing containing: a liquid supply component comprising: a chamber providing a reservoir for liquid providing an active ingredient to be supplied to a user and means for supplying liquid from the reservoir to a liquid outlet (liquid supplying means); and means for creating an electric field (electric field creating means) for causing comminution of liquid issuing from the liquid supplying means outlet in response to air flowing through the air inlet so as to produce a stream of electrically charged comminuted matter for supply to the nasal passages via the housing outlet.

2. An inhaler according to claim 1, wherein the liquid supplying means has first and second outlets; and the electric field creating means comprises a first electrohydrodynamic comminution means for subjecting liquid issuing from the first outlet to an electrical potential to cause liquid to be comminuted to form a comminution of one polarity; and a second electrohydrodynamic comminution means for subjecting liquid issuing from the second outlet to an electrical potential to cause the liquid to be comminuted to form a comminution of the opposite polarity, means being provided for providing an air flow to the outlet to modify any mixing of the two opposite polarity comminutions.

3. An inhaler according to claim 1, wherein the electric field creating means comprises first and second spaced apart electrodes with the first electrode being provided at or adjacent the outlet of the liquid supplying means; and voltage supplying means operable in response to air flowing through the air inlet to provide a potential difference between the first and second electrodes.

4. An inhaler according to claim 3, wherein the voltage supplying means comprises an air flow activated switch for coupling a voltage generating means across the first and second electrodes.

5. An inhaler according to claim 3, wherein the air flow activated switch comprises a closure member and spring biassing means normally biassing the closure member into a position closing off the supply of air into the housing through the air inlet, the closure member being movable against the spring biassing to a position allowing air to flow into the housing through the air inlet in response to the air flow.

6. An inhaler according to claim 1, wherein the housing is arranged to enable a user to create the air flow by breathing in through the housing outlet.

7. An inhaler according to claim 1, further comprising a pump for creating the air flow.

8. An inhaler according to claim 1, wherein the electric field creating means comprises: first and second spaced apart electrodes with the first electrode being provided at or adjacent the outlet of the liquid supplying means; and user-operable voltage supplying means for providing a potential difference between the first and second electrodes to create the electric field for causing comminution of liquid issuing from the liquid supplying means outlet to produce a stream of electrically charged comminuted matter, the first and second electrodes being spaced from the housing outlet and being arranged so as to provide, when a potential difference is applied across them by the voltage supplying means, and electric field which reduces rapidly in the direction of liquid flow from the liquid supplying means and the housing having an air flow path to the housing outlet for causing liquid comminuted by the electric field to be entrained by the air flow for supply via the housing outlet to the nasal passages of a user.

9. An inhaler according to claim 3, wherein the first and second spaced apart electrodes are spaced apart in a direction perpendicular to a flow of liquid from the liquid supplying means.

10. An inhaler according to claim 3, wherein the second electrode is located downstream of the liquid outlet.

11. An inhaler according to claim 1, wherein the electric field creating means comprises: first and second spaced apart electrodes with the first electrode being provided at or adjacent the outlet of the liquid supplying means; and user-operable voltage supplying means for providing a potential difference between the first and second electrodes to create the electric field for causing comminution of liquid issuing from the liquid supplying means outlet to produce a stream of electrically charged comminuted matter for supply via the housing outlet to the nasal passages of a user, wherein current-limiting means are provided for limiting the supply of current by the voltage supplying means.

12. An inhaler according to claim 11, wherein current-limiting means is coupled to one of the first and second electrodes.

13. An inhaler according to claim 11, wherein the current-limiting means comprises a dielectric or semi-insulating coating or sleeve provided on said one of the first and second electrodes.

14. An inhaler according to claim 8, wherein the voltage supplying means comprises an air flow activated switch for coupling a voltage generating means across the first and second spaced apart electrodes.

15. An inhaler according to claim 14, wherein the air flow activated switch comprises a closure member and spring biassing means normally biassing the closure member into a position closing off the supply of air into the housing through the air inlet, the closure member being movable against the spring biassing to a position allowing air to flow into the housing through the air inlet in response to a user breathing in through the housing outlet or in response to an air supply to the air inlet.

16. An inhaler according to claim 3, wherein the voltage supplying means comprises a further electrode positioned adjacent the second electrode and resistive means coupling the second electrode to earth, the voltage supplying means being arranged to cause the further electrode to generate an ion current for charging the second electrode to an electrical potential sufficient to provide the electrical potential for causing comminution of liquid issuing from the outlet.

17. An inhaler according to claim 1, further comprising: means for providing a flow of air towards the housing outlet so as to supply the stream of electrically charged comminuted matter to the nasal passages of a user via the housing outlet.

18. An inhaler according to claim 1, further comprising: means for shearing comminuted matter (shearing means) issuing from the liquid outlet to produce a stream of electrically charged comminuted matter of smaller size than that produced by the electric field for supply to the nasal passages of a user via the housing outlet.

19. An inhaler according to claim 18, wherein the shearing means comprises means for producing airflow in the vicinity of liquid issuing form the liquid outlet.

20. An inhaler according to claim 1, wherein the liquid supplying means comprises means for supplying liquid to first and second outlets; and the electric field creating means has a first electrohydrodynamic comminution means for subjecting liquid issuing from the first outlet to an electrical potential to cause the liquid to be comminuted to form a comminution of one polarity; a second electrohydrodynamic comminution means for subjecting liquid issuing from the second outlet to an electrical potential to cause the liquid to be comminuted to form a comminution of the opposite polarity; and means for providing an air flow to the outlet to modify any mixing of the two opposite polarity comminutions.

21. An inhaler according to claim 2, wherein the air flow providing means is operable to keep the two opposite polarity comminutions apart.

22. An inhaler according to claim 2, further comprising means for controlling at least one of: 1) the relative flow rates of liquid to the first and second liquid outlets; 2) the relative electrical potentials to which liquid issuing from the first and second outlets is subjected; and 3) the air flow provided by the air flow providing means.

23. An inhaler according to claim 2, comprising a respective reservoir for each liquid outlet, the reservoirs containing different liquids.

24. An inhaler according to claim 2, wherein the first and second liquid outlets are angled towards one another.

25. An inhaler according to claim 1, further comprising air flow control valve means for controlling the air flowing.

26. An inhaler according to claim 1, further comprising: means for controlling the size of the components of the comminuted matter.

27. An inhaler according to claim 1, further comprising: means for controlling the size of the comminuted matter such that the communited matter has at least two different controlled sizes.

28. An inhaler according to claim 1, further comprising means for controlling the diameter of the droplets so that the comminuted matter consists of droplets each having one of at least two different controlled diameters.

29. An inhaler according to claim 22, wherein the controlling means comprises means for superimposing on the voltage supplied by the voltage supplying means an alternating or pulsed signal (superimposing means).

30. An inhaler according to claim 22, wherein the controlling means comprises means for superimposing on the voltage supplied by the voltage supplying means a signal having two different frequency components for causing the comminuted matter to contain two different sizes of components (superimposing means).

31. An inhaler according to claim 29, wherein the superimposing means is arranged to superimpose on the voltage supplied by said voltage supplying means a signal having three or more different frequency components for causing the comminuted matter to contain three or more different sizes of components.

32. An inhaler according to claim 30, wherein said signal is arranged to consist of said frequency components superimposed simultaneously on said voltage in phase with one another.

33. A device according to claim 30, wherein said signal is arranged such that said different frequency components are superimposed one after another on said voltage.

34. An inhaler according to claim 25, wherein the means for controlling the size of the components of the comminution comprises means for regulating the liquid flow and/or the liquid composition.

35. An inhaler according to claim 25, wherein the means for controlling the size of the comminution components comprises a plurality of subsidiary liquid outlets which together form the liquid outlet and respective different cross-section supply pipes for supplying liquid to each different one of the subsidiary liquid outlets.

36. An inhaler according to claim 25, wherein the means for controlling the size of the comminution components comprises a plurality of subsidiary liquid outlets which together form the liquid outlet each having a respective valve means for controlling the liquid flow from the outlet.

37. An inhaler according to claim 1, having a respective housing outlet for each nostril of a user or patient.

38. An inhaler according to claim 1, wherein the air flow is induced other than by inhalation.

39. An inhaler according to claim 1, comprising a biologically acceptable carrier for the active ingredients selected from: an oil, an alcohol, a polymer or a water-based solvent.

40. An inhaler according to claim 1, comprising a supply of liquid carrying as an active ingredient at least one of the following: a decongestant, a lipid, a vitamin, an antiseptic, an anti-inflammatory, an antibiotic, an anti-cancer agent, a vaccine, a protein, an enzyme, a bioadhesive, DNA or DNA fragments, nicotine and morphine.

41. A liquid formulation for use in an inhaler in accordance with claim 1, comprising a biologically acceptable carrier liquid for an active ingredient and a polymer.

42. A liquid formulation according to claim 41, wherein the polymer is a medium to high molecular weight polymer.

43. A liquid formulation according to claim 41, wherein the polymer is PVA or PVP.

44. A liquid formulation according to claim 41, wherein the polymer is selected from amongst the following: 0.2 to 0.7 grams per 10 centiliters of formulation of PVA; 0.2 grams per 10 centiliters of formulation of PVA; from 0.2 to 1.2 grams per 10 centiliters of formulation of PVP; or 0.5 grams per 10 centiliters of formulation of PVP.

45. A liquid formulation according to claim 41, further comprising as an active ingredient at least one of the following: a decongestant, a lipid, a vitamin, an antiseptic, an anti-inflammatory, an antibiotic, an anti-cancer agent, a vaccine, a protein, an enzyme, a bioadhesive, DNA or DNA fragments, nicotine and morphine.

46. A delivery device according to claim 1, but differing in that the device is arranged to supply the active ingredient to the mouth, an eye or a bodily orifice and in that air flow is induced other than by inhalation or alternatively by oral inhalation when the device is arranged to supply the active ingredient to or via the mouth.

47. A method of supplying an active ingredient to the nasal passages of a human or animal which comprises using an inhaler in accordance with claim 1.

48. A method of supplying an active ingredient to an eye or bodily orifice other than the mouth or nose which comprises using a delivery device in accordance with claim 46.

49. An inhaler according to claim 26, wherein the components include droplets.

50. A dispensing device comprising a housing having an outlet and an air inlet, the housing containing liquid supplying means comprising:

a chamber providing a reservoir for liquid providing an active ingredient to be supplied to a user and means for supplying liquid from the reservoir to a liquid outlet; and means for creating an electric field for causing comminution of liquid issuing from the liquid supplying means outlet in response to air flowing through the air inlet so as to produce a stream of electrically charged comminuted matter for supply to the housing outlet, the housing outlet being adapted to supply the comminuted matter containing the active ingredient to at least one of the mouth and eye and a bodily orifice of the user.

* * * * *

UNITED STATES PATENT AND TRADEMARK OFFICE
CERTIFICATE OF CORRECTION

PATENT NO. : 6,684,879 B1
DATED : February 3, 2004
INVENTOR(S) : Ronald Alan Coffee et al.

It is certified that error appears in the above-identified patent and that said Letters Patent is hereby corrected as shown below:

<u>Title page,</u>
Item [56], References Cited, FOREIGN PATENT DOCUMENTS, "WO 9440441" should be -- WO 9640441 --.

Signed and Sealed this

Fifteenth Day of June, 2004

JON W. DUDAS
*Acting Director of the United States Patent and Trademark Office*